US007109310B2

(12) United States Patent
McConnell et al.

(10) Patent No.: US 7,109,310 B2
(45) Date of Patent: Sep. 19, 2006

(54) METHOD AND KIT FOR DETECTING, OR DETERMINING THE QUANTITY OF, METABOLITES OF FENTANYL AND METABOLITES OF FENTANYL ANALOGS

(75) Inventors: Robert Ivan McConnell, Ballymena (GB); Elouard Benchikh, Antrim (GB); Stephen Peter Fitzgerald, Crumlin (GB); John Victor Lamont, Crumlin (GB)

(73) Assignee: Randox Laboratories, Ltd., Antrim (IE)

( * ) Notice: Subject to any disclaimer, the term of this patent is extended or adjusted under 35 U.S.C. 154(b) by 547 days.

(21) Appl. No.: 10/295,700

(22) Filed: Nov. 15, 2002

(65) Prior Publication Data

US 2003/0170728 A1 Sep. 11, 2003

(30) Foreign Application Priority Data

Nov. 16, 2001 (EP) .................................. 01204401

(51) Int. Cl.
*C07K 16/44* (2006.01)
*C12N 9/96* (2006.01)
*G01N 33/533* (2006.01)
*G01N 33/534* (2006.01)
*G01N 33/535* (2006.01)

(52) U.S. Cl. ..................... 530/405; 435/7.93; 435/188; 436/545; 436/546; 530/388.9; 530/389.8

(58) Field of Classification Search ............... 435/7.93, 435/188; 530/405, 389.8, 388.9; 436/545, 436/546

See application file for complete search history.

(56) References Cited

FOREIGN PATENT DOCUMENTS

WO WO 96/39425 12/1996

OTHER PUBLICATIONS

G. Makowski et al, Annals of Clinical and Laboratory Science (1995), vol. 25, No. 2, pp. 169-178.*
Burke, T.R. et al., "Probes for Narcotic Receptor Mediated Phenomena. 7. Synthesis and Pharmacological Properties of Irreversible Ligands Specific for .mu. or delta. Opiate Receptors", *J. Med. Chem*, 1984, 27(12), 1570-1574.
Camu, F. et al., "Pharmacokinetics of Alfentanil in Man", *Anesth. Analg.*, 1982, 61, 657-661.
Chappey, O.N. et al., "Monoclonal Antibodies in Hapten Immunoassays", *Pharmaceutical Research*, 1992, 9(11), 1375-1379.
Frincke, J.M. et al., "The Major Metabolite of Fentanyl in the Horse", *Drug Metabolism and Disposition*, 1980, 8(6), 425-427.
Hammargen, W.R. et al., "Analyzing Normetabolites of the Fentanyls by Gas Chromatography/Electron Capture Detection", *Journal of Analytical Toxicology*, 1988, 12(4), 183-191.

Henderson, G.L. et al, "Antibodies to Fentanyl", *The Journal of Pharmacology and Experimental Therapeutics*, 1975, 192(2), 489-496.
Henderson, G.L. et al., "Metabolism and Disposition of Fentanyl in Man and the Horse", *Proc. West Pharmacol. Soc.*, 1981, 24, 137-140.
Lobbezoo, M.W. et al., "Structure and receptor interactions of morphinomimetics. Part I. Hydroxy and methoxy derivatives of fentanyl and some morphine analogues", *Eur. J. Med. Chem. Chim. Ther.*, 1980, 15(4), 357-361.
Makowski, G.S. et al., "An enzyme-linked immunosorbent assay for urinary screening of fentanyl citrate abuse", XP-002206131, 1995, 1 page.
Maryanoff, B.E. et al., "Potential Affinity Labels for the Opiate Receptor Based on Fentanyl and Related Compounds", *Journal of Medical Chemistry*, 1982, 25(8), 913-919.
McDonald, J. et al., "Immunoassay Detection of Drugs in Horses I. Particle Concentration Fluoroimmunoassay Detection of Fentanyl and Its Congeners", *Research Communications in Chemical Pathology and Pharmacology*, 1987, 57(3), 389-407.
Meuldermans, W.E.G. et al., "Plasma Protein Binding and Distribution of Fentanyl, Sufentanil, Alfentanil and Lofentanil in Blood", *Arch Int Pharmacodyn*, 1982, 257, 4-19.
Michiels, M. et al., "Radioimmunoassay of the new opiate amalgesics alfentanil and sufentanil. Preliminary pharmacokinetic profile in man", 1983, XP-002206132, 1 page.
Michiels, M. et al., "A Sensitive Radioimmunoassay for Fentanyl", *Europ. J. Clin. Pharmacol*, 1977, 12, 153-158.
Rosner, M.H. et al., "Immunochemical Techniques in Biological Monitoring", *Environmental Health Perspectives*, 1991, 94, 131-134.
Ruangyuttikarn, W. et al., "Detection of Fentanyl and its Analogs by Enzyme-Linked Immunosorbent Assay", *Journal of Analytical Toxicology*, 1990, 14(3), 160-164.
Silverstein, J.H., "An analysis of the duration of fentanyl and its metabolites in urine and saliva", 1993, XP-002206130, 1 page.
Watts, V.W. et al., "Evaluation of the Coat-a-Count 125 I Fentanyl RIA: Comparison of 125I RIA and GC/MS-SIM for Quantification of Fentanyl in Case Urine Specimens", *Journal of Analytical Toxicology*, 1990, 14(5), 266-272.
Woods, W.E. et al., "High-sensitivity radioimmunoassay screening method for fentanyl", *Am J Vet Res*, 1986, 47(10), 2180-2183.

* cited by examiner

*Primary Examiner*—Mary E. Ceperley
(74) *Attorney, Agent, or Firm*—Woodcock Washburn LLP

(57) ABSTRACT

The invention provides an immunogen comprising a hapten coupled to an antigenicity-conferring carrier material, a conjugate comprising the aforementioned hapten coupled to a labelling agent, as well as, antibodies raised against the aforementioned immunogen and capable of binding with at least one structural epitope of metabolites of fentanyl and of metabolites of fentanyl analogs.

50 Claims, 16 Drawing Sheets

R=OH, Hapten F
R=NHBSA, Immunogen F

Figure 6: BSA Carrier Material

Figure 7: Bromoacetylglycine Modified BSA Carrier Material

Figure 8: Hapten A Conjugated to Bromoacetylglycine Modified BSA

Figure 9: Hapten C Conjugated to Bromoacetylglycine Modified BSA

Figure 10. Hapten F Conjugated to BSA

Figure 11: Hapten G Conjugated to BSA

Figure 12: Competitive ELISA microtiter plate assay

METHOD AND KIT FOR DETECTING, OR DETERMINING THE QUANTITY OF, METABOLITES OF FENTANYL AND METABOLITES OF FENTANYL ANALOGS

The present invention relates to a method and kit for detecting, or determining the quantity of, metabolites, preferably nor-metabolites, both of fentanyl and of its analogs, as well as, immunogens, conjugates and antibodies useful therein.

By "detecting" is meant qualitatively analysing for the presence or absence of a substance.

By "determining" is meant quantitatively analysing for the amount of a substance present.

By "fentanyl" is meant N-(1-phenethyl-4-piperidinyl)-N-phenylpropionamide.

By "fentanyl analogs" is meant substances sharing structural similarity with the N-phenyl-N-(4-piperidinyl) amine structure of fentanyl and sharing pharmacological activity with fentanyl. Such "fentanyl analogs" include, but are not limited to, sufentanil, carfentanil, acetylfentanyl, p-fluorofentanyl, benzylfentanyl, thienylfentanyl, α-methylthienylfentanyl, butyrylfentanyl and alfentanil as well as, the so-called designer drugs, ∝- and p-methylfentanyl and 3-cis/trans-methylfentanyl.

By "metabolites" is meant the breakdown products, in vivo, both of fentanyl and of fentanyl analogs. Thus, for fentanyl, this embraces nor-fentanyl (N-(propionyl)-4-N-anilinopiperidine), despropionyl fentanyl (N-(1-phenethyl-4-piperidinyl)-phenylamine), p-hydroxyfentanyl (N-(p-hydroxyphenyl)-N-[1-(2-phenylethyl)-4-piperidinyl] propanamide) and p-hydroxy nor-fentanyl (N-propionyl-4-N-(p-hydroxyanilino) piperidine).

The present invention is intended to have broad applicability across metabolites, both of fentanyl and of fentanyl analogs. The present invention is intended to have particular applicability to nor-metabolites, both of fentanyl and of fentanyl analogs. The present invention is intended to have most particular applicability to nor-metabolites of fentanyl. The present invention is also intended to have broad applicability across fentanyl itself and its analogs.

Fentanyl is a powerful synthetic opioid with at least 80 times the potency of morphine as an analgesic. It is routinely used peri-operatively for the induction and maintenance of anaesthesia and postoperatively for analgesia. Analogs of fentanyl have been synthesised for increasing its analgesic and euphoric effect. Due to their high potency and fast-acting narcotic analgesia, fentanyl and its analogs have abuse potential. Fentanyl distributes rapidly from blood to body tissues and is extensively metabolized. In man, approximately 80% of a fentanyl dose is excreted in urine within 72 hours, with 92% to 98% of this consisting of metabolites. Oxidative N-dealkylation to form nor-fentanyl is the major metabolic pathway for fentanyl in man (Silverstein et al, 1993). N-dealkylation also seems characteristic of fentanyl analogs such as alfentanil and sufentanil (Camu et al (1982) and Meuldermans et al (1982)). In contrast, in horses, the major metabolic pathway is via metabolic oxidation of the propionyl side chain of fentanyl, to form a malonanilinic acid (Frincke et al (1980)). The chemical structure of fentanyl is represented below:

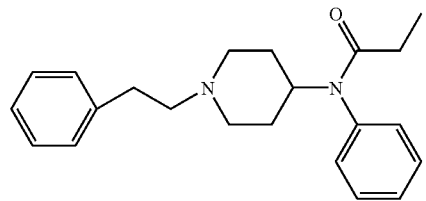

Fentanyl, which has a half life of 10 minutes, is metabolized, at least in humans, to yield mainly:

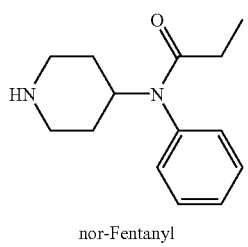

nor-Fentanyl

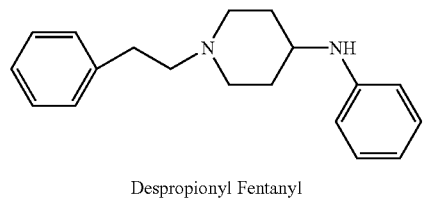

Despropionyl Fentanyl

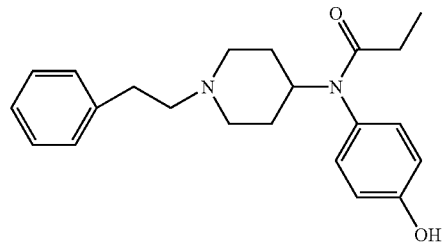

p-Hydroxy Fentanyl

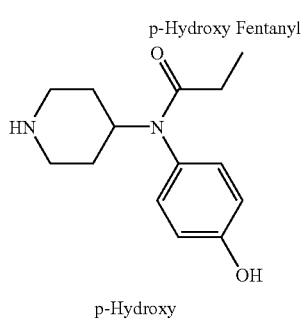

p-Hydroxy nor-Fentanyl

Various methods have been used to determine the quantity of metabolites of fentanyl, and its analogs in a sample. Analytical methods include gas chromatography with flame ionisation, electron capture, and nitrogen sensitive detection, and gas chromatography/mass spectrometry (GC/MS). For example, a sensitive gas-liquid chromatographic method for analyzing the nor-metabolites of fentanyl and 3-methylfentanyl in urine is disclosed in W. R. Hammargren and G. L. Henderson, 1988. The method disclosed includes detection by electron capture detector or mass spectroscopy. Such chromatographic methods are, however, too costly and time consuming for use as screening tools.

Radioimmunoassays used for the determination of the quantity of fentanyl and its analogs are very sensitive, but do require radionuclide tracers, for example $^{125}$I and $^{3}$H, and in some cases, a preliminary extraction step. For example, various different types of radioimmunoassays (RIAs), including solid phase RIA, are used to detect fentanyl and related analogs. Hammargren & Henderson (1988) disclose use of a $^{125}$I RIA produced by Diagnostic Products. However, it was found that the normetabolites and despropionylmetabolites do not cross-react significantly using the radioimmunoassay. In addition, Watts & Caplan (1990) disclose a fentanyl RIA (also a $^{125}$I RIA from Diagnostic Products), which confirms the data of Hammargren & Henderson (1988), namely, with poor cross-reactivity for certain fentanyl metabolites, specifically less than 5% (Table IV response analog/response fentanyl) for norfentanyl and 14–30% (Table IV response analog/response fentanyl) for 2-hydroxyfentanyl. Concerning 2-hydroxyfentanyl, it is currently believed that this is not a major metabolite of fentanyl, at least in man, despite the reference thereto in Watts & Caplan. Michiels et al (1977) disclose a $^{3}$H RIA for fentanyl from Janssen using carboxyfentanyl as the hapten—no cross-reaction was observed with despropionyl fentanyl and nor-fentanyl, the major metabolites of fentanyl in humans. Similarly, Henderson et al (1975) disclose a fentanyl RIA from McNeil Laboratories using carboxyfentanyl as the hapten but all the nor- and despropionyl-metabolites of fentanyl do not cross-react significantly.

Enzyme-linked immunosorbent assays (ELISAs) are a nonradioactive alternative, which are also known for the determination of the quantity of fentanyl, and its analogs. For example, in Werawan Ruangyuttikarn et al, 1990, a prototype ELISA is disclosed for detecting the presence of fentanyl using a carboxyfentanyl hapten. This disclosure, whilst explicitly silent on cross-reactivity against metabolites of fentanyl, teaches that modification about the piperidine moiety dramatically alters cross-reactivity—this suggests that poor cross-reactivity could be expected for nor-fentanyl. Gregory S. Makowski et al, 1995 discloses an ELISA with poor cross reactivity against despropionyl fentanyl and nor-fentanyl metabolites, specifically, only 0.53% cross-reactivity against despropionyl fentanyl and less than 0.03% cross-reactivity against nor-fentanyl.

Previously reported work on fentanyl immunoassays (whether RIA or ELISA) has solely centred, to the knowledge of the inventors, on derivatization of fentanyl (by a carboxyl group) through the free end of the propionamide group of fentanyl. Such a derivatisation, using —COOH as the crosslinker, results in carboxyfentanyl (N-phenyl-N-[1-(2-phenethyl)-4-piperidinyl]carboxypropanamide) as the hapten, which hapten is disclosed in J. McDonald et al, 1987. J. McDonald et al disclose a particle concentration fluorescence immunoassay (PCFIA) using an antiserum raised from a carboxyfentanyl-bovine serum albumin (BSA) immunogen and carboxyfentanyl linked to b-Phycoerythrin. Similarly, M Michiels et al (1977) disclose a carboxyfentanyl-BSA immunogen. Antibodies raised to a carboxyfentanyl-bovine gamma globulin (BGG) immunogen are disclosed in GL Henderson et al, 1975. However, antibodies and conjugates raised against carboxyfentanyl as the hapten suffer from the disadvantage that there is little or no ability to detect metabolites of fentanyl and/or metabolites of fentanyl analogs.

BIBLIOGRAPHY

Camu et al; Anesth. Analg.; 61; pp 657–61 (1982)
Frincke, J. M. & Henderson, G. L.; Drug Metab. Dispos.; 8(6); pp 425–7 (1980).
Hammargren, W. R. & Henderson, G. L.; J. Anal. Toxicol.; 12; pp 183–191 (1988).
Henderson et al; J. Pharmacol. Exp. Ther.; 192 (2); pp 489–96 (1975).
Makowski et al; Annals of Clinical and Laboratory Science; 25 (2); pp 169–177 (1995).
McDonald et al; Res. Commun. Chem. Pathol. Pharmacol.; 57 (3); pp 389–407 (1987).
Meuldermans et al; Arch. Int. Pharmacodyn. Ther.; 257; pp 4–19 (1982).
Michiels et al; Eur. J. Clin. Pharmacol.; 12 (2); pp 153–8 (1977).
Ruangyuttikarn et al; J. Anal. Toxicol.; 14; pp 160–164 (1990).
Silverstein et al; Anesthesia and Analgesia; 76; pp 618–621 (1993).
Watts, V. W. & Caplan, Y. H.; J. Anal. Toxicol; 14; pp 266–272 (1990).

SUMMARY OF THE INVENTION

The present invention describes bonding of a novel hapten derivative of fentanyl or norfentanyl, the hapten being covalently linked either to an antigenicity-conferring carrier material, in order to produce an immunogen, or to a detectable labelling agent, in order to produce a conjugate (or detection reagent). The present invention also describes how antibodies generated to this immunogen are employed in the development of a generic assay, which can be used to determine the quantity of metabolites of fentanyl, and metabolites of its analogs, in fluids, preferably biological fluids, more preferably in biological fluids from humans.

The invention describes haptens which are derivatised using a crosslinker at positions schematically illustrated as $R_1$, $R_2$, $R_3$ and $R_4$ on accompanying FIG. 1a, with the proviso that $R_1$ is not carboxyl. In addition, the invention claims an immunogen comprising certain of the aforementioned haptens coupled to an antigenicity-conferring carrier material; a conjugate comprising certain of the aforementioned haptens coupled to a detectable labelling agent; as well as, antibodies raised against the aforementioned immunogen and capable of binding with at least one structural epitope of metabolites of fentanyl and of metabolites of fentanyl analogs.

The invention further provides a method and a kit for detecting, or determining the quantity of, metabolites of fentanyl and metabolites of fentanyl analogs, as well as, use of the aforementioned conjugate with the aforementioned antibodies for detecting, or determining the quantity of, metabolites of fentanyl and metabolites of fentanyl analogs.

The present invention has broad specificity across various metabolites of fentanyl and various metabolites of fentanyl analogs.

OBJECTS OF THE INVENTION

It is an object of the invention to overcome some or all of the disadvantages of the prior art, or to provide an alternative thereto.

It is an object of a preferred embodiment of the invention to provide a method and a kit for detecting, or determining the quantity of, metabolites of fentanyl and/or metabolites of fentanyl analogs. It is an object of a more preferred embodiment of the invention to provide a method and a kit for detecting, or determining the quantity of, metabolites of fentanyl and/or metabolites of fentanyl analogs, showing more than 5%, preferably more than 25%, cross-reactivity for the metabolites of fentanyl and/or the metabolites of fentanyl analogs, more preferably the nor-metabolites, when compared to fentanyl itself.

It is a further object of a preferred embodiment of the present invention to develop antibodies capable of binding with, as a structural epitope, an N-phenyl-N-(4-piperidinyl) amine moiety.

DETAILED DESCRIPTION OF INVENTION

Figure 1:
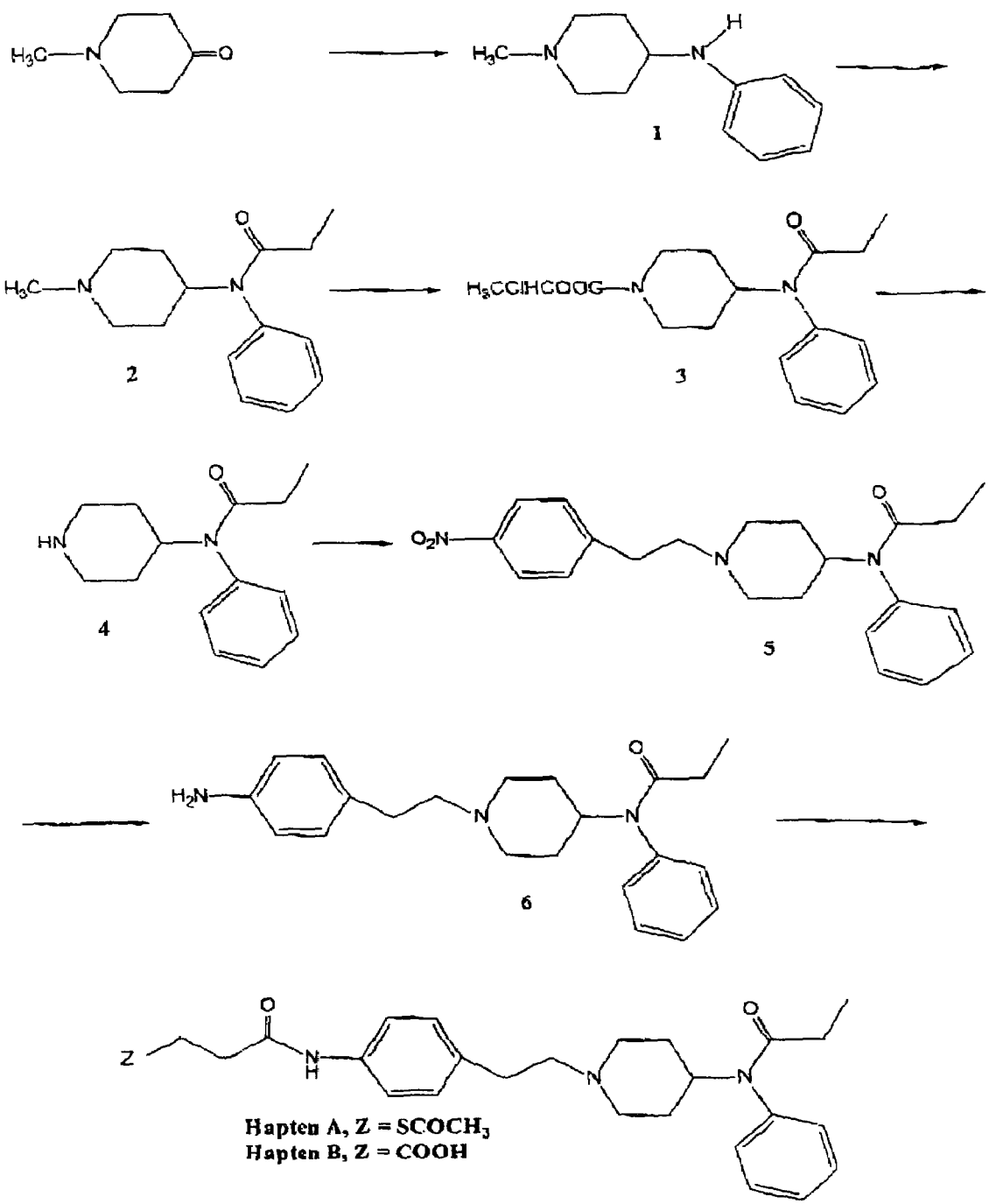
FIG. 1 shows a reaction scheme for the preparation of Haptens A and B.

In a first aspect, the invention provides an immunogen comprising a hapten coupled to an antigenicity-conferring carrier material, the hapten being derivatised with a crosslinker at position 1, 2 or 4, preferably at position 1 or 2, with the proviso that the crosslinker is not carboxyl when the hapten is derivatised at position 1.

Position 1 is defined as the free or terminal end of the propionamide group of fentanyl. Position 2 is defined as the para position of the phenethyl group of fentanyl. Position 3 is defined as the para position of the N-phenyl group of fentanyl. Position 4 is defined as the piperidinyl-N of norfentanyl. Positions 1–4 are designated as $R_1$–$R_4$, respectively in FIG. 1a of the accompanying drawings.

Derivatisation positions 1, 2, 3 and 4 of the haptens described in the present invention are indicated below having regard to the structural formulae of fentanyl or nor-fentanyl:

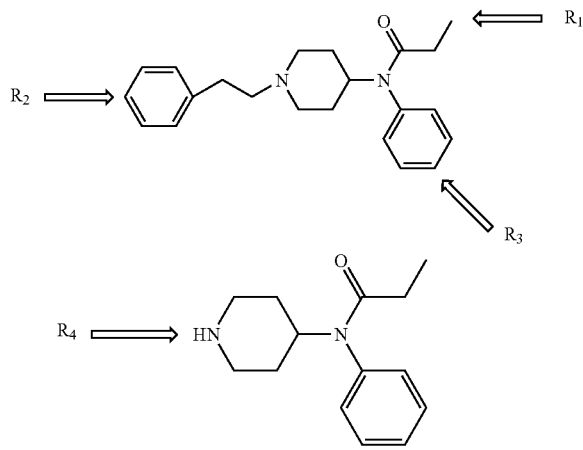

More specifically, in a first aspect, the invention provides an immunogen of the formula:

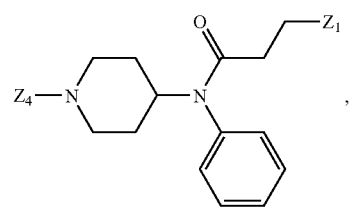

wherein $Z_1$ is a crosslinker coupled to an antigenicity-conferring carrier material or hydrogen; $Z_4$ is selected from N-phenethyl, a crosslinker coupled to an antigenicity-conferring carrier material or

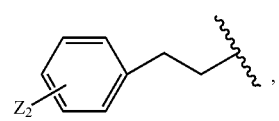

wherein $Z_2$ is a crosslinker coupled to an antigenicity-conferring carrier material at an ortho, a meta or a para position, with the provisos that, when $Z_1$ is hydrogen, $Z_4$ is a crosslinker coupled to an antigenicity-conferring carrier material or

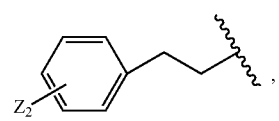

wherein $Z_2$ is a crosslinker coupled to an antigenicity-conferring carrier material at an ortho, a meta or a para position; and, when $Z_4$ is N-phenethyl, $Z_1$ is a crosslinker coupled to an antigenicity-conferring carrier material, the crosslinker not being —COOH. Preferably, the carrier material is a protein, a protein fragment, a synthetic polypeptide or a semi-synthetic polypeptide.

In a further aspect, the present invention comprises a conjugate of the formula:

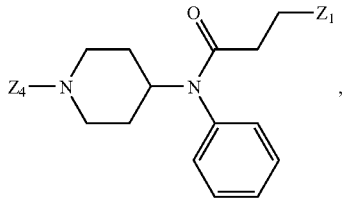

wherein $Z_1$ is a crosslinker covalently bonded to a detectable labelling agent, or hydrogen; $Z_4$ is selected from N-phenethyl, a crosslinker covalently bonded to a detectable labelling agent or

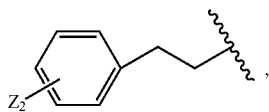

wherein $Z_2$ is a crosslinker covalently bonded to a detectable labelling agent at an ortho, a meta or a para position, with the provisos that, when $Z_1$ is hydrogen, $Z_4$ is a crosslinker covalently bonded to a detectable labelling agent or

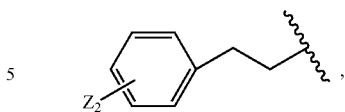

wherein $Z_2$ is a crosslinker covalently bonded to a detectable labelling agent at an ortho, a meta or a para position; and, when $Z_4$ is N-phenethyl, $Z_1$ is a crosslinker covalently bonded to a detectable labelling agent, the crosslinker not being —COOH. Preferably, the labelling agent is selected from an enzyme, a luminescent substance, a radioactive substance, or a mixture thereof. More preferably, the labelling agent is an enzyme, preferably a peroxidase, most preferably horseradish peroxidase. Alternatively, or additionally, the luminescent substance may be a bioluminescent, chemiluminescent or fluorescent material.

It will be appreciated that, in the haptens described in the present invention, just one of the $Z_1$, $Z_2$ and $Z_4$ positions is a crosslinker and that, in immunogens and conjugates of the present invention, just one of the $Z_1$, $Z_2$ and $Z_4$ positions includes a crosslinker covalently linked to either an antigenicity-conferring carrier material or to a detectable labelling agent, respectively.

It will also be appreciated that, when $Z_1$ is hydrogen and $Z_4$ is N-phenethyl, the resultant compound is fentanyl and, when $Z_1$ and $Z_4$ are each hydrogen, the resultant compound is nor-fentanyl.

Table 1 hereunder summarises the crosslinkers and derivatisation positions for certain of the haptens described in the present invention and for certain of the immunogens and conjugates of the present invention:

TABLE 1

Chemical structures of certain haptens derived from fentanyl and from its metabolite, nor-fentanyl.

| DERIVATIVES | $Z_1$ | $Z_2$ | $Z_4$ |
|---|---|---|---|
| HAPTEN A | H | —NH—C(O)—CH$_2$CH$_2$—S—C(O)—CH$_3$ | phenethyl-$Z_2$ |
| HAPTEN B | H | —NH—C(O)—CH$_2$CH$_2$—CO$_2$H | phenethyl-$Z_2$ |
| HAPTEN C | —S—C(O)—CH$_3$ | H | phenethyl-$Z_2$ |
| HAPTEN D | —CO$_2$H | H | phenethyl-$Z_2$ |
| HAPTEN E | —CH$_2$CH$_2$—CO$_2$H | H | phenethyl-$Z_2$ |
| HAPTEN G | H | | —CH$_2$CH$_2$—CO$_2$H |

Preferably, the crosslinker of $Z_2$ is at the para position.

Preferably, the crosslinker of $Z_1$, $Z_2$ or $Z_4$ terminates, at its free end, with —CO—R, wherein R is hydroxyl or a short chain, straight or branched chain, alkyl moiety. By "short chain alkyl" is meant a $C_{1-5}$ moiety. More preferably, the short chain alkyl moiety is a straight chain moiety. Even more preferably, the short chain alkyl moiety is a $C_{1-2}$ moiety, preferably a $C_{1-2}$ straight chain alkyl moiety.

More preferably, the crosslinker of $Z_1$, $Z_2$ or $Z_4$ comprises:

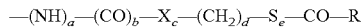

wherein a is 0 or 1; b is 0 or 1; X is oxygen or sulfur; c is 0 or 1; d is selected from the integers 1–5; e is 0 or 1 and R is a short chain alkyl moiety, preferably a $C_{1-5}$ straight or branched chain alkyl moiety, or a hydroxy moiety. More preferably, the alkyl moiety is a $C_{1-5}$ straight chain moiety. Still more preferably, the alkyl moiety is a $C_{1-2}$ straight chain moiety. Most preferably, the alkyl moiety is methyl.

The last provisos in the statements of invention, in their broadest aspect, for an immunogen or conjugate of the present invention, namely, that the $Z_1$ crosslinker is not carboxyl (—COOH) covalently linked to either an antigenicity-conferring carrier material or to a detectable labelling agent, respectively, means that the above-mentioned crosslinker formula excludes a crosslinker wherein a, b, c, d and e are 0 and R is hydroxyl, when $Z_1$ is the crosslinker.

Preferably, when e is 1, c is 0.

Preferably a is 0; b is 0; and c is 0. More preferably, d is 0; e is 1 and R is methyl or, alternatively, d is 1; c is 0; and R is hydroxyl. More preferably, $Z_1$ or $Z_4$ is such a crosslinker. Alternatively, $Z_2$ could be such a crosslinker.

Alternatively, a is 1; b is 1; c is 0; and d is 2. Preferably, e is 1; and R is methyl or, alternatively, e is 0; and R is hydroxyl. More preferably, $Z_2$ is such a crosslinker at an ortho, a para or a meta position, preferably a para position. Alternatively, $Z_1$ or $Z_4$ could be such a crosslinker.

Further alternatively, a is 0; b is 0; e is 0; X is 0; and c is 1. Preferably, d is 3; and R is hydroxyl. $Z_1$, $Z_2$ or $Z_4$ could be such a crosslinker.

The invention further provides a process of preparing the antibodies, the process comprising the steps of immunising an animal, preferably a vertebrate animal, most preferably a mammalian animal, by repeated administration of an immunogen according to a first aspect of the present invention, and collecting the resulting serum from the immunised animal. Preferably, the process further comprises fixing said serum antibodies to a backing substrate, preferably a solid support, most preferably a polystyrene solid support. Antibodies prepared in accordance with this process are polyclonal.

In a still further aspect, the present invention concerns antibodies raised against the immunogen of the present invention, the antibodies being capable of binding with at least one structural epitope of a metabolite of fentanyl or of a metabolite of its analogs. Preferably, the at least one structural epitope comprises the N-phenyl-N-(4-piperidinyl) amine structure of fentanyl. More preferably, the antibodies are fixed on a backing substrate.

The invention preferably concerns the production of avid polyclonal antisera to metabolites of fentanyl and to metabolites of its analogs, which antisera, most preferably, also exhibit some cross-reactivity with fentanyl and its analogs.

wherein wherein wherein

In a still further aspect, the present invention comprises a method for detecting, or determining the quantity of, metabolites of fentanyl, and metabolites of fentanyl analogs in a sample, the method comprising contacting the sample with the conjugate of the present invention, or a mixture thereof, and with antibodies of the present invention, or a mixture thereof, detecting, or determining the quantity of, bound conjugate; and deducing from a calibration curve the presence, or the amount of, metabolites of fentanyl and metabolites of fentanyl analogs in the sample.

In a further aspect, the invention includes a kit for detecting, or determining the quantity of, metabolites of fentanyl, and metabolites of fentanyl analogs, the kit including the conjugate of the present invention, or a mixture thereof and the antibodies of the present invention, or a mixture thereof. The kit may optionally include instructions for the use of said conjugates and said antibodies for detecting, or determining the quantity of, metabolites of fentanyl and metabolites of fentanyl analogs in a sample.

Preferably, the sample is a solution, such as a biological fluid. More preferably, the sample is serum or urine. Most preferably, the sample is a solution or a suspension from a human patient.

The method or kit of the present invention comprises a conjugate, or a mixture thereof, in which the or each conjugate is prepared from a hapten in which one of $Z_1$, $Z_2$ or $Z_4$, preferably one of $Z_2$ or $Z_4$, is a crosslinker and an antibody, or a mixture thereof, in which the or each antibody is generated to a hapten, in which one of $Z_1$, $Z_2$ or $Z_4$, preferably one of $Z_1$ or $Z_2$, is a crosslinker. The respective constituent haptens may be identical or the respective constituent haptens may be derivatised at the same position but using different crosslinkers, the latter being preferred. However, it is preferred that the respective constituent haptens be derivatised at different positions, either using the same crosslinkers or using different crosslinkers. More preferred, is an immunogen derived from a hapten in which $Z_2$ is a crosslinker for use in a method or kit of the present invention with a conjugate derived from a hapten in which one of $Z_2$ or $Z_4$ is a crosslinker, in which the respective crosslinkers (of the immunogen and the conjugate) are the same or, more preferably, different. Preferred, is an immunogen derived from a hapten in which $Z_2$ is a crosslinker for use in a method or kit of the present invention with the conjugate derived from a hapten in which $Z_4$ is a crosslinker, in which the respective crosslinkers (of the immunogen and the conjugate) are the same or, more preferably, different.

Equally contemplated, is a conjugate derived from a hapten in which $Z_2$ or $Z_4$ is a crosslinker for use in a method or kit of the present invention with an immunogen derived from a hapten in which one of $Z_1$, $Z_2$ or $Z_4$ is a crosslinker, in which the respective crosslinkers (of the immunogen and the conjugate) are the same or, more preferably, different. Still more preferred, is a conjugate derived from a hapten in which $Z_2$ or $Z_4$ is a crosslinker for use in a method or kit according to the present invention, with an immunogen derived from a hapten in which one of $Z_1$ or $Z_2$ is a crosslinker. Most preferred, is a conjugate derived from a hapten in which $Z_2$ or $Z_4$ is a crosslinker for use in a method or kit of the present invention with an immunogen derived from a hapten in which $Z_2$ is a crosslinker, in which the respective crosslinkers (of the immunogen and the conjugate) are the same, or, more preferably, different.

In a further aspect, the present invention involves use of the conjugates according to the present invention, or a mixture thereof, with the antibodies according to the present invention, or a mixture thereof, to test samples such as biological fluids, for detecting, or determining the quantity of, metabolites of fentanyl and metabolites of fentanyl analogs.

The present invention relates to novel haptens, which are employed in the preparation of novel immunogens by conjugation to conventional antigenicity-conferring carrier materials. The resulting immunogen is then administered to animals, preferably vertebrate hosts, most preferably mammalian hosts, to elicit production of avid polyclonal antisera which are then used to develop a generic immunoassay for metabolites of fentanyl and for metabolites of fentanyl analogs, employing a conjugate (hapten—detectable labelling agent) as the detection reagent.

The focus of the present invention is the preparation of antibodies specific for metabolites of fentanyl and for metabolites of fentanyl analogs. In order to achieve such broad specificity, haptens and immunogens are generated by modification of fentanyl using $Z_1$ or $Z_2$ as the crosslinker, and by modification of norfentanyl using $Z_4$ as the crosslinker.

Preparation of Haptens

Figure 1A:
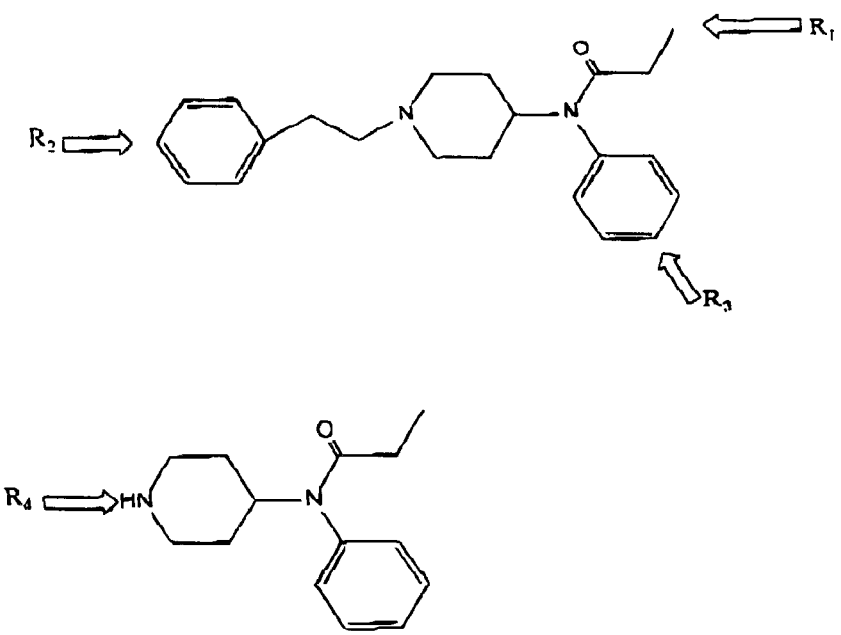
FIG. 1a shows the derivatisation positions of haptens described herein.

Preparation of haptens A and B is performed according to reaction scheme 1 set out in FIG. 1. Preparation of haptens C, D and E is performed according to reaction scheme 2 set out in FIG. 2. Preparation of hapten F and immunogen F is performed according to reaction schemes 3 and 4 set out in FIGS. 3 and 4 and preparation of hapten G and immunogen G is performed according to reaction scheme 5 set out in FIG. 5.

Referring to FIG. 1, haptens N-[1-(p-acetylthiopropionamido)phenethyl-4-piperidinyl]-N-phenylpropionamide (A) and N-[1-(p-succinamido)phenethyl-4-piperidinyl]-N-phenylpropionamide (B) are prepared according to reaction scheme-1. A condensation reaction between aniline and N-methyl-4-piperidone, via Schiff base formation, in the presence of 1,2-dichloroethane, acetic acid and NaBH(OAc)$_3$ results in the production of compound 1. This compound reacts with propionic anhydride, in the presence of toluene and under reflux to produce compound 2. Norfentanyl (compound 4) is prepared by N-dismethylation of compound 2, in a two step process, using in the first step, 1-chloroethylchloroformate (ClCO$_2$CHClCH$_3$) in the presence of 1,2-dichloroethane, under reflux for 2 hours and, in the second step, methanol. Reaction of compound 4 with p-nitrophenethylbromide in the presence of 4-methyl-2-pentanone and K$_2$CO$_3$ under reflux; followed by reduction of the nitro group to an amino group using Pd—C in the presence of HCOONH$_4$ and CH$_3$OH results in production of intermediate compound 6. Hapten A is produced by reaction of compound 6 with N-succinimidyl 3-(acetylthio)propionate (SATP) in the presence of EDPA and dioxane and hapten B is produced by reaction of compound 6 with succinic anhydride.

Figure 2:
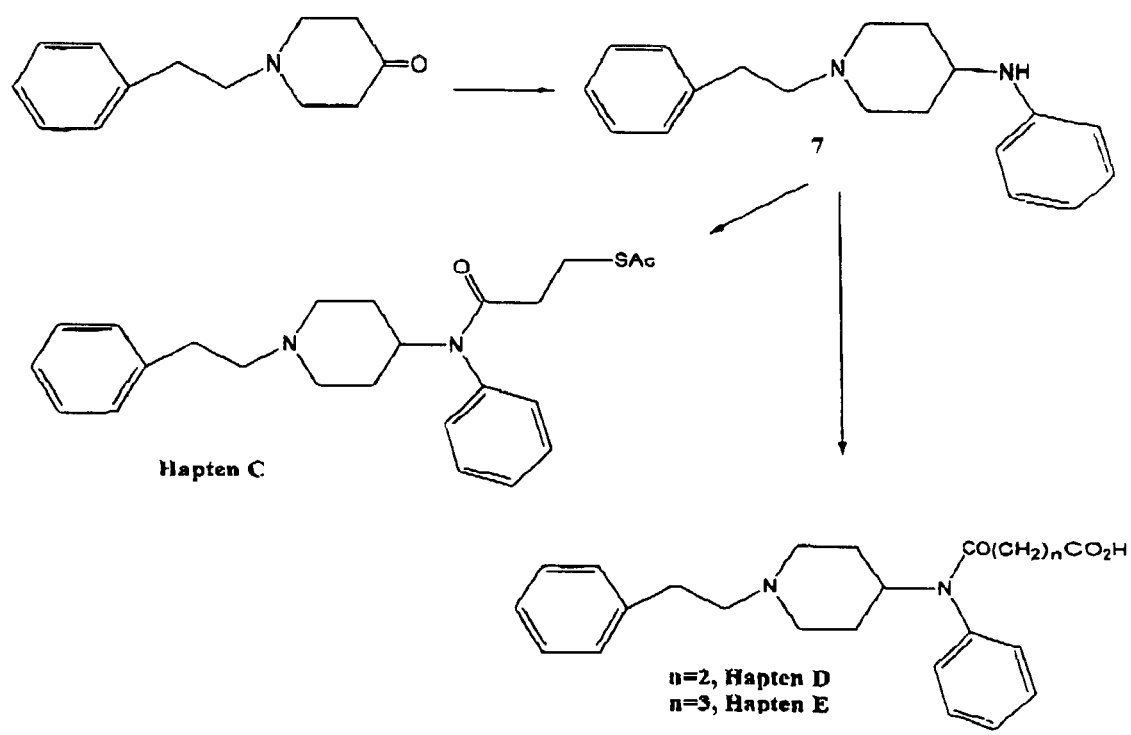
FIG. 2 shows a reaction scheme for the preparation of Haptens C, D and E.

Referring to FIG. 2, the haptens N-(1-phenethyl-4-piperidinyl)-N-phenyl(S-acetylthiopropionamide) (C), N-(1-phenethyl-4-piperidinyl)-N-phenylsuccinamide (D) and N-(1-phenethyl-4-piperidinyl)-N-phenylglutaramide (E) are prepared according to reaction scheme-2. Despropionyl fentanyl (compound 7) is prepared by reaction of 1-phenethyl-4-piperidone with aniline followed by reduction of the Schiff base. The compound produced is then reacted with N-succinimidyl 3-(acetylthio)propionate (SATP) in the presence of EDPA and dioxane to yield hapten C, with succinic anhydride to yield hapten D or with glutaric anhydride to yield hapten E.

Figure 3:
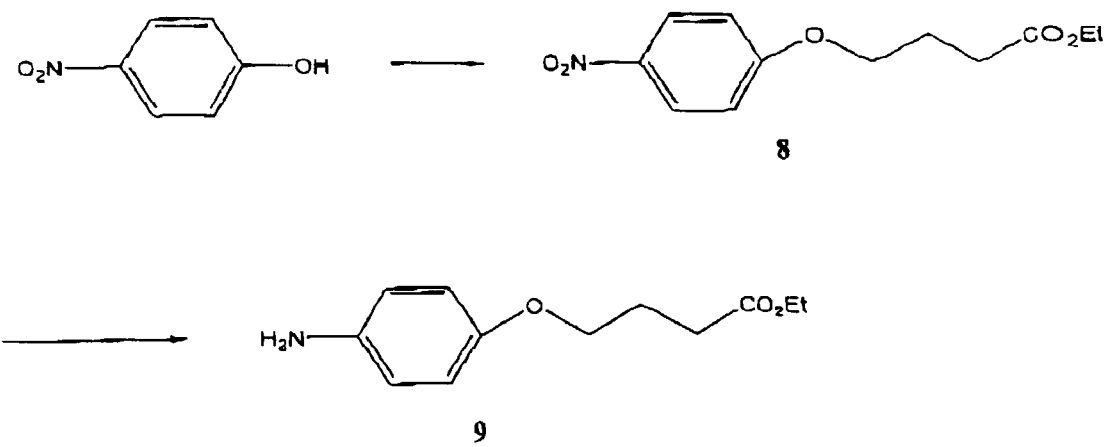
FIGS. 3 and 4 shows reaction schemes for the preparation of Hapten F and Immunogen F.
Figure 4:
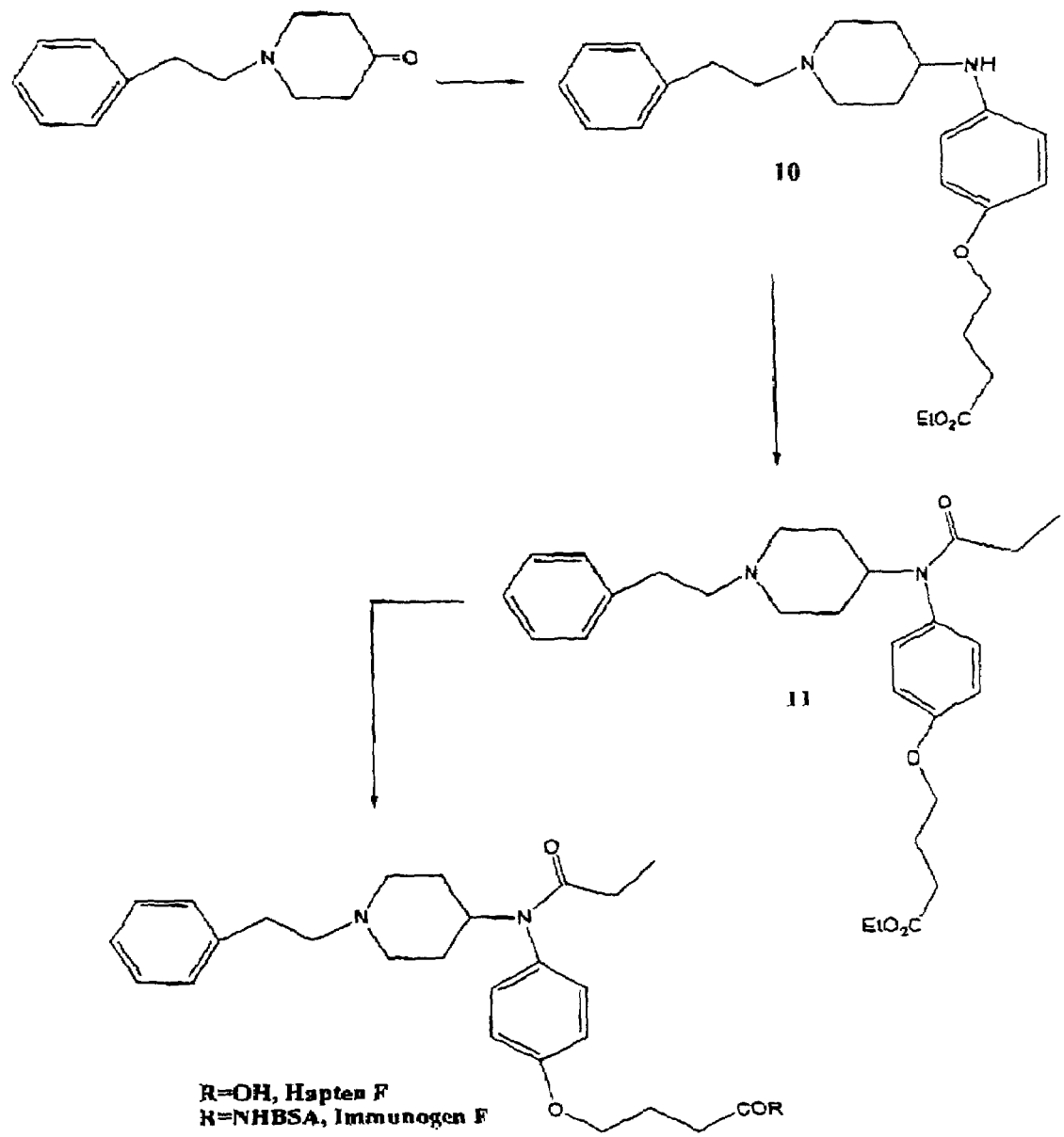

Referring to FIGS. 3 and 4, prior to the preparation of the hapten N-(1-phenethyl-4-piperidinyl)-N-(p-O-carboxypropyl)-phenylpropionamide (F), [ethyl-p-(O-carboxypropyl)] aniline (compound 9) is generated according to reaction scheme-3 of FIG. 3. p-nitrophenol is alkylated with ethyl-4-bromobutyrate in the presence of sodium hydride to produce compound 8. The nitro group of compound 8 is then reduced to an amino group using Pd—C, resulting in the production of compound 9.

N-(1-phenethyl-4-piperidinyl)-N-(p-O-carboxypropyl)-phenylpropionamide (hapten F) is prepared in three steps according to reaction scheme-4 of FIG. 4. N-(1-phenethyl)-4-piperidone is reacted with [ethyl-p-(O-carboxypropyl)] aniline (compound 9) in 1,2-dichloroethane, in the presence of sodium triacetoxyborohydride and acetic acid, to produce compound 10. Compound 10 reacts with propionic anhydride in toluene under reflux to yield compound 11. Hapten F is produced by saponification of compound 11 with 2N sodium hydroxide in methanol.

Figure 5:
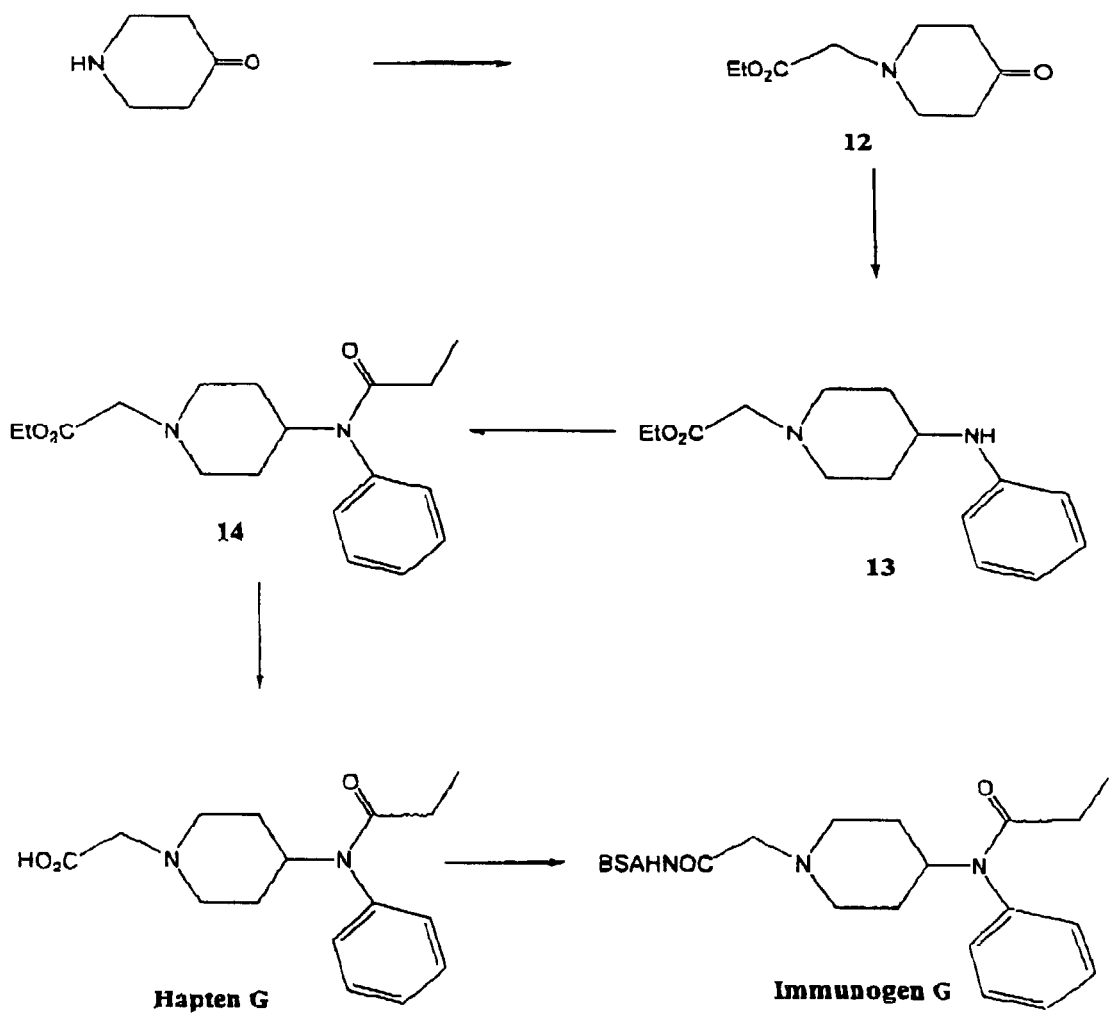
FIG. 5 shows a reaction scheme for the preparation of Hapten G and Immunogen G.

Referring to FIG. 5, the hapten N-(1-carboxymethyl-4-piperidinyl) N-phenylpropionamide (G) is prepared in four steps according to reaction scheme-5. Reaction of 4-piperidone monohydrate monohydrochloride with ethyl bromoacetate in the presence of sodium hydride in DMF yields ethyl-N-carboxymethyl-4-piperidone (compound 12). Compound 12 is then reacted with aniline in the presence of sodium triacetoxyborohydride and acetic acid to produce N-(ethyl-1-carboxymethyl-4-piperidinyl)-N-phenylalanine (compound 13). Compound 13 is treated with propionic anhydride in toluene under reflux to yield compound 14. Hapten G is produced by saponification of compound 14 with sodium hydroxide (2N) in methanol.

Preparation of Immunogens and Conjugates

Although the fentanyl haptens provide defined structural epitopes, they are not in themselves immunogenic and therefore need to be conjugated to carrier material, which will elicit an immunogenic response when injected into a host animal. Suitable carrier materials include proteins such as albumins, serum proteins e.g. globulins, ocular lens proteins and lipoproteins. Illustrative protein carriers include bovine serum albumin, egg ovalbumin, bovine gamma globulin, thyroxine binding globulin, keyhole limpet haemocyanin etc. Alternatively, synthetic poly(amino acids) having a sufficient number of available amine groups such as lysine may be employed, as may other synthetic or natural polymeric materials bearing reactive functional groups. In particular, carbohydrates, yeasts or polysaccharides may be conjugated to the hapten to produce an immunogen.

Each hapten can also be covalently linked to a labelling group such as an enzyme (for example, horse radish peroxidase), a substance having fluorescent properties or a radioactive label to produce conjugates (also known as detection reagents) for use in the immunoassays. The fluorescent substance may be, for example, a monovalent residue of fluorescein or a derivative thereof.

In order to confirm that adequate conjugation of hapten to carrier material has been achieved, prior to immunisation, each immunogen is evaluated using matrix-assisted UV laser desorption/ionization time-of-flight mass spectrometry (MALDI-TOF MS). In the case of the preferred carrier material, bovine serum albumin, a minimum of 6 molecules of hapten per carrier molecule is preferred.

In preparing conjugates or immunogens with haptens where e, in the crosslinker, is 1 such as, for example, haptens A and C, maleimide, halo, mercaptopyridyl, or vinylsulphone groups must first be introduced to the labelling agent or carrier material, respectively, using heterobifunctional linkers such as, but not limited to: N-(γ-maleimidobutyryloxy)succinimide ester (GMBS); succinimidyl 4-(N-maleimidomethyl)cyclohexane-1-carboxylate (SMCC); (m-maleimidobenzoyl)-N-hydroxysuccinimide (MBS); succinimidyl 4-(p-maleimidophenyl)butyrate (SMPB); N-succinimidyl(4-iodoacetyl)aminobenzoate (SIAB); bromoacetylglycine N-hydroxysuccinimide; N-succinimidyl 3-(2-pyridyldithio)propionate (SPDP); vinylsulphone (Pierce Chemical Company, USA). The thus-modified labelling agent or carrier material, can then be conjugated via the thiol groups on haptens in which e is 1, such as haptens A and C. For haptens where e, in the crosslinker, is 0, such as haptens B, D, E, F and G, conjugation is performed without prior-modification of labelling agent or carrier material, as appropriate, using standard methods of conjugation such as EDC or mixed anhydride.

Preparation of Antisera

In order to generate polyclonal antisera, the immunogen is mixed with Freund's Adjuvant and the mixture is injected into a host animal, such as a rabbit, sheep, mouse, guinea pig or horse. Further injections (boosts) are made and serum is sampled for evaluation of antibody titer. When the optimal titer has been reached, the host animal is then bled to yield a suitable volume of specific antiserum. The degree of antibody purification required depends on the intended application. For many purposes, there is no requirement at all for purification, however, in other cases, such as where the antibody is to be immobilized on a solid support, purification steps can be taken to remove undesired material and eliminate non specific binding.

The specific antibodies of the present invention are useful as reagents in biochemical assays for the detection, or for the determination of the amount of, metabolites of fentanyl and metabolites of its analogs in biological fluids.

In the following table, the results of characterising data for compounds prepared in the following Examples 4, 6–11 and 13–15 are set out:

| Compound | Melting Point (° C.) | FT IR (KBr, Diffuse Reflectance, cm$^{-1}$) |
|---|---|---|
| Example 6 | 154–157 | 3479.64, 3360.85, 1648.53 and 1594.23 |
| Example 7 (Hapten A) | 164–167 | 3322.61, 1687.21, 1627.29 and 1594.98 |
| Example 4 | 94–96 | 3426.96, 1648.67 and 1594.62 |
| Example 9 | 92–94 | 3286.45, 1601.08 |
| Example 8 (Hapten B) | 222–225 | 3244.1, 3180.1, 1677.7, 1648.7 and 1597.1 |
| Example 10 (Hapten C) |  | 1687.02, 1627.42 and 1536.36 |
| Example 11 (Hapten D) | 198–202 | 1714.06, 1650.94 and 1595 |
| Example 11 (Hapten E) | 141–142 | 3442.02, 1654.13 and 1596.14 |
| Example 13 | 198–200 | 3330.98, 1735.92, 1614.7 and 1514.78 |
| Example 14 | 183–185 | 1730.99, 1654.98 and 1509.46 |
| Example 15 (Hapten F) | 113 (Decomp) | 3228, 1716.1, 1647.9 and 1510 |

General Procedure for MALDI-TOF Analysis of Immunogens

Figure 6:
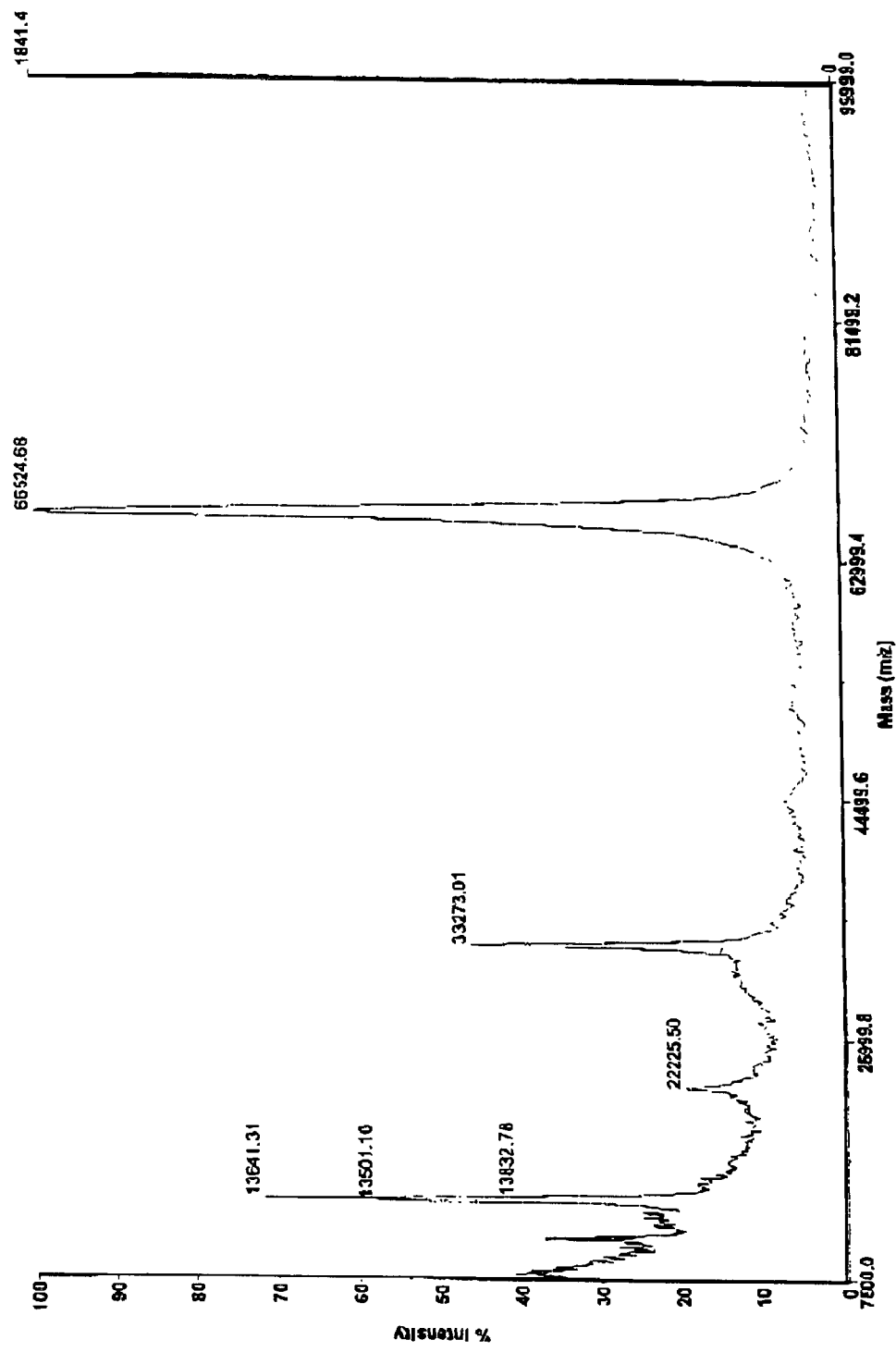
FIG. 6 shows MALDI-TOF analysis of BSA carrier material.

MALDI-TOF mass spectrometry was performed using a Voyager STR Biospectrometry Research Station laser-desorption mass spectrometer coupled with delayed extraction. An aliquot of each sample to be analysed was diluted in 0.1% aqueous trifluoroacetic acid (TFA) to create 1 mg/ml sample solutions. Aliquots (1 µl) were analysed using a matrix of Sinapinic acid and bovine serum albumin (Fluka) was used as an external calibrant. FIG. 6 of the accompanying drawings shows the analysis for BSA carrier material. As will be seen, a major signal was present which indicates an average protonated mass for this sample of m/z 66,525. The signal at m/z 33,273 is consistent with the major component in a doubly-charged form and further signals were observed including that at m/z 13,641.

In the following examples, all percentages are v/v unless otherwise specified.

EXAMPLE 1

Reaction Scheme 1

Preparation of N-(1-methyl)-4-(phenylamine)piperidine (Compound 1)

To a solution of 4-N-methyl-1-piperidone (7 g, 0.0062 mol) in 100 ml of anhydrous 1,2-dichloroethane, was added aniline (12.7 g, 0.14 mol) and acetic acid (4 ml), followed by sodium triacetoxyborohydride (13.1 g, 0.062 mol). The mixture was stirred at room temperature under nitrogen overnight.

After evaporation of the solvent under reduced pressure, water (100 ml) was added and the solution was made alkaline by adding NaOH (1N), to pH 9. The solution was then extracted using toluene (2×100 ml), the organic layers combined and washed with water (150 ml), brine (50 ml), dried over sodium sulfate, filtered and concentrated under reduced pressure. The residue was chromatographed (silica gel, 5% MeOH/chloroform) to give 9.4 g (80% yield) of compound 1 as a white solid after recrystallization from ethyl acetate.

EXAMPLE 2

Reaction Scheme 1

Preparation of N-(1-methyl-4-piperidinyl)-N-phenylpropionamide (Compound 2)

To a solution of compound 1 of Example 1 (9.0 g, 0.047 mol) in anhydrous toluene (150 ml), was added propionic anhydride (15.4 g, 0.118 mol). The mixture was stirred overnight at reflux. The solvents were removed in vacuo and the residue recrystallized from ethyl acetate/hexane to give 10 g of compound 2 as a white solid (86% yield).

EXAMPLE 3

Reaction Scheme 1

Preparation of N-[1-(1'-ethylchloroformate)-4-piperidinyl]-N-phenylpropionamide (Compound 3)

10 g (0.04 mol) of compound 2 of Example 2 was dissolved in anhydrous 1,2-dichloroethane (100 ml), under a nitrogen atmosphere, and cooled to 0° C. in an ice-bath. To this solution was added, dropwise, 1-chloroethyl chloroformate (6.6 g, 0.046 mol) and the solution heated at reflux for 2 hours (thin layer chromatography indicated when reaction was complete). The solution was cooled to room temperature and the solvents removed under reduced pressure. The viscous oily residue was purified by column chromatography (silica gel, 10% ethyl acetate/90% n-hexane) to give the title compound as a white amorphous solid (10 g, 74% yield).

EXAMPLE 4

Reaction Scheme 1

Preparation of norfentanyl (Compound 4)

10 g (0.03 mol) of compound 3 of Example 3 was dissolved in anhydrous methanol (150 ml) and stirred overnight at room temperature. The solution was concentrated under reduced pressure to give the title compound as a white powder in quantitative yield.

EXAMPLE 5

Reaction Scheme 1

Preparation of N-[1-(p-nitrophenethyl)-4-piperidinyl]-N-phenylpropionamide (Compound 5)

A suspension of norfentanyl of Example 4 (6.71 g, 0.029 mol), p-nitrophenethylbromide (7.178 g, 0.0372 mol), potassium carbonate (19 g, 0.14 mol) and a few crystals of sodium iodide in 4-methyl-2-pentanone (200 ml) was stirred overnight at reflux, under nitrogen. After cooling to room temperature, the precipitate was removed by filtration and the solution concentrated under reduced pressure. The dark residue was dissolved in ethyl acetate (200 ml) and washed with water (2×100 ml), dried over sodium sulfate, filtered and the solvent removed in vacuo. The residue was purified by column chromatography (silica gel, 10% MeOH/90% $CHCl_3$ v/v) to give the title compound as a yellow solid (5.33 g, 56% yield).

EXAMPLE 6

Reaction Scheme 1

Preparation of N-[1-p-aminophenethyl)-4-piperidiny]-N-phenylpropionamide (Compound 6)

To a stirring solution of compound 5 of Example 5 (5 g, 0.013 mol) in anhydrous methanol (200 ml) was added, under a nitrogen atmosphere, 10% Pd—C (650 mg) followed by ammonium formate (5 g, 0.063 mol). The mixture was stirred at room temperature for 4 hours and filtered through a short column of Celite™ to remove the catalyst. The solvent was removed under reduced pressure and the residue taken up in water (100 ml). The aqueous solution was made alkaline by the addition of 1N NaOH and extracted with ethyl acetate (2×100 ml). The organic layers were combined, washed with water (50 ml), brine (50 ml) and dried over anhydrous sodium sulfate. The solution was then concentrated under reduced pressure to produce compound 6, a white powder exhibiting a single spot on thin layer chromatography (2.7 g, 60% yield).

Figure 13:
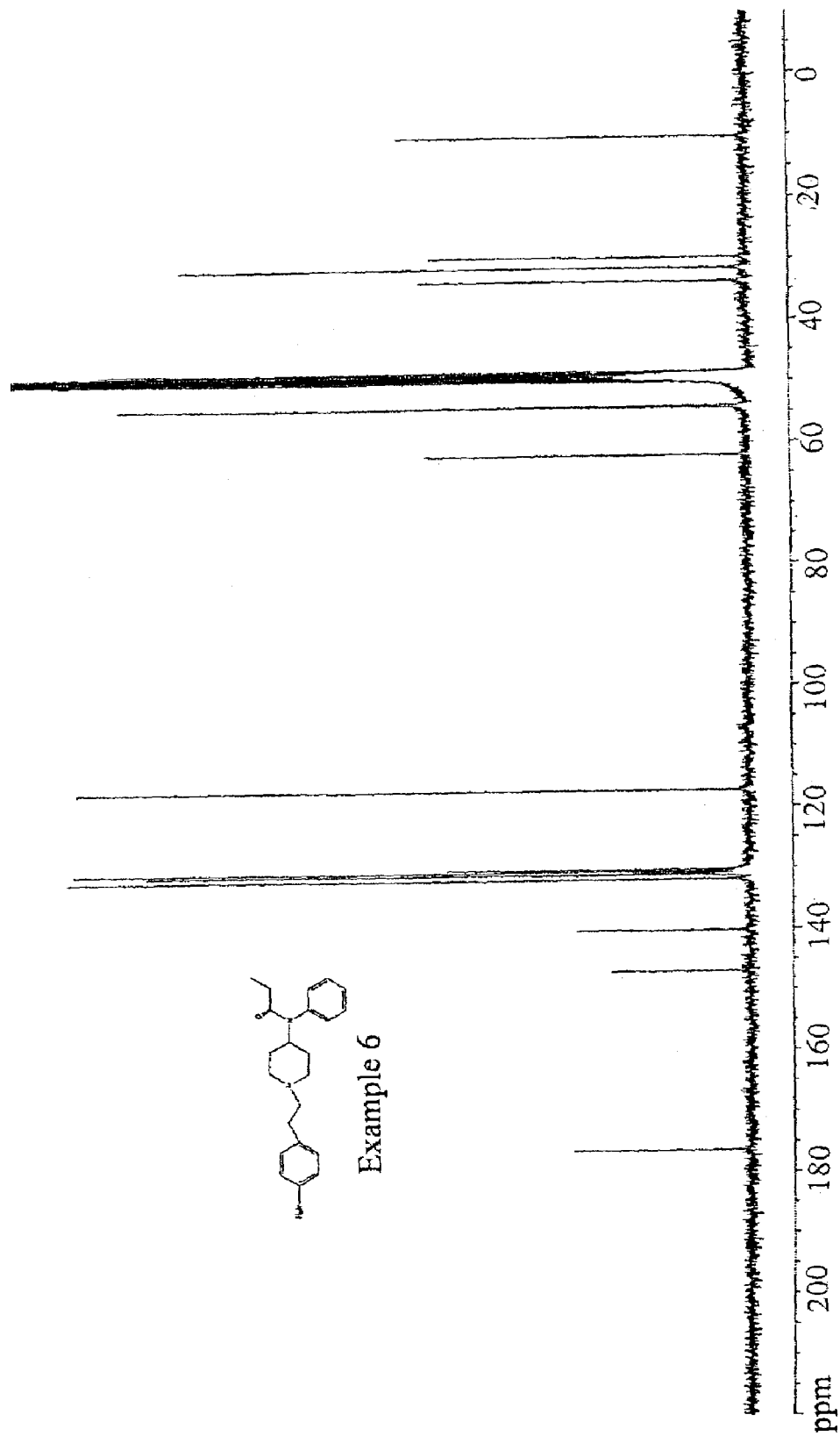
FIG. 13 shows NMR$^{13}$C data for Compound 6 of Example 6.

NMR data for compound 6 are presented in FIG. 13.

EXAMPLE 7

Reaction Scheme 1

Preparation of N-[1-(p-acetylthiopropionamido)phenethyl-4-piperidinyl]-N-phenylpropionamide (Hapten A)

To a stirring solution of compound 6 of Example 6 (1 g, 0.0028 mol) and N-succinimidyl 3-(acetylthio)propionate (SATP) (0.824 g, 0.00336 mol ) in 25 ml of anhydrous dioxane under nitrogen was added diisopropylethylamine (EDPA) (0.72 ml, 0.0042 mol), and the mixture was stirred and heated at 60° C. for 6 hrs. The mixture was then concentrated in vacuo and the residual was purified by flash chromatography on silica gel using 10% v/v methanol in chloroform to produce hapten A, a white solid which was recrystallized from hexane chloroform in the cold (835 mg, 62% yield).

Figure 14:
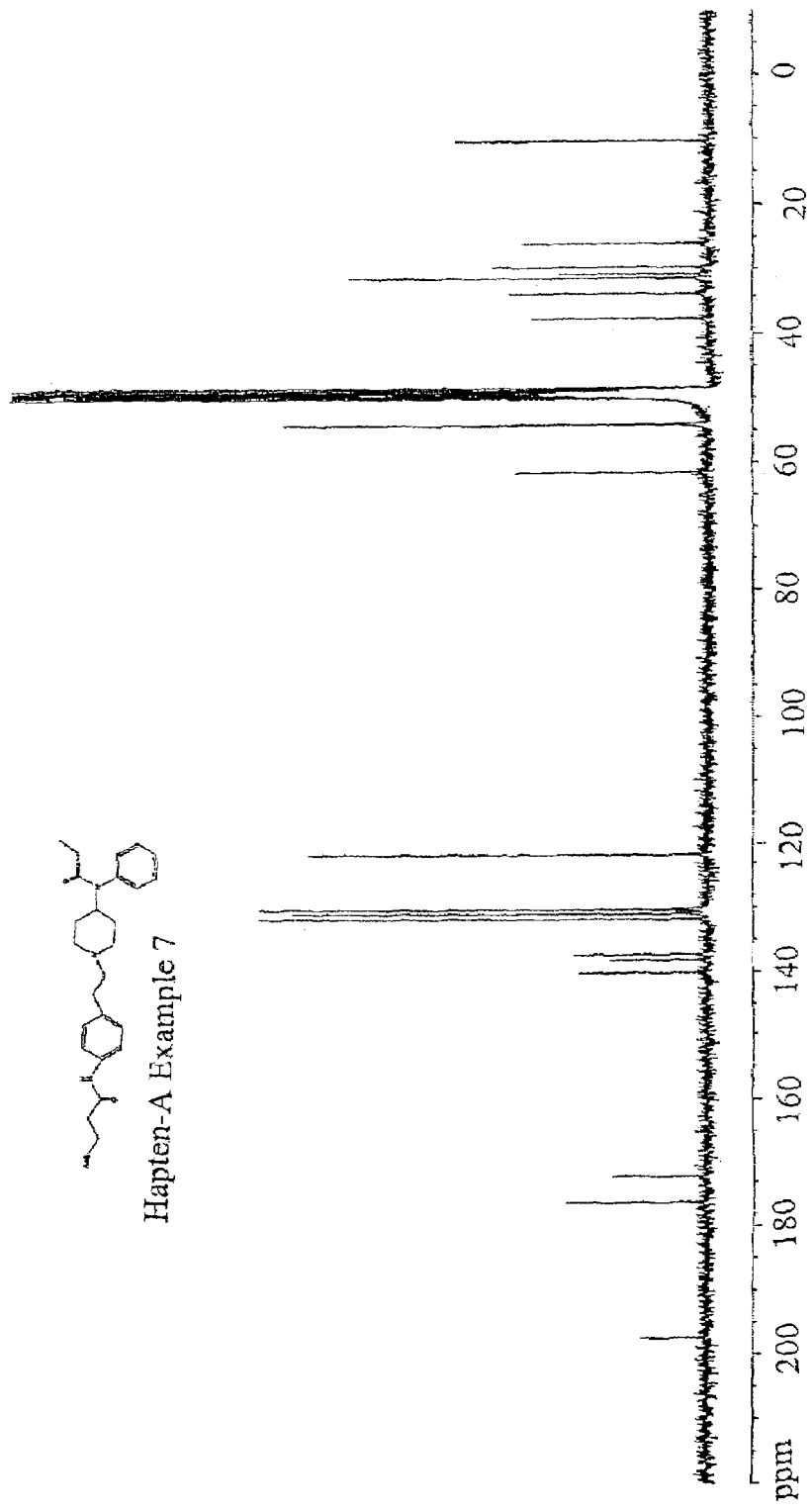
FIG. 14 shows NMR$^{13}$C data for Hapten A.

NMR Data for Hapten A are presented in FIG. 14.

EXAMPLE 8

Reaction Scheme 1

Preparation of N-[1-(p-succinamido)phenethyl-4-piperidinyl]-N-phenylpropionamide (Hapten B)

To a solution of compound 6 of Example 6 (1 g, 0.0028 mol) in anhydrous benzene (75 ml) was added succinic anhydride (0.7007 g, 0.007 mol) and the mixture was refluxed overnight A white precipitate was produced and TLC confirmed that all starting material had been consumed. The precipitate was filtered off, washed with benzene and dried. It was taken up in water (20 ml) and heated at 50° C. for one hour, filtered and thoroughly dried. The solid was taken up in acetonitrile (20 ml) and heated at 60° C. for one hour, filtered, washed with a little cold acetonitrile and dried under vacuum overnight to give the title compound as a white solid (0.82 g, 60% yield).

EXAMPLE 9

Reaction Scheme 2

Preparation of N-(1-phenethyl-4-piperidinyl)-phenylamine (despropionylfentanyl) (Compound 7)

The title compound was prepared by the method outlined in Example 1 using 1-phenethyl-4-piperidone (5.3 g, 0.026 mol), aniline (5.01 ml, 0.55 mol), acetic acid (3 ml) 1,2-dichloroethane (100 ml) and sodium triacetoxyborohydride (5.82 g, 0.027 mol). The title compound was obtained as a white solid (74% yield).

EXAMPLE 10

Reaction Scheme 2

Preparation of N-(1-phenethyl-4-piperidinyl)-N-phenyl-(S-acetylthiopropionamide) (Hapten C)

Hapten C was prepared by the same method outlined in Example 7 with 55% yield, i.e., with N-succinimidyl 3-(acetylthio) propionate (SATP) in anhydrous dioxane, to which diisopropylethylamine (EDPA) is added.

EXAMPLE 11

Reaction Scheme 2

Preparation of Haptens D and E

Haptens D and E were prepared by the same method outlined in Example 8. Hapten D was prepared using succinic anhydride (2 eq) and Hapten E prepared using glutaric anhydride (2 eq).

EXAMPLE 12

Reaction Scheme 3

Preparation of [Ethyl-p-(O-carboxypropyl)]aniline (Compound 9)

To a suspension of sodium hydride (3.696 g, 0.11 mol) in 100 ml of anhydrous dimethylformamide under nitrogen, was added dropwise p-nitrophenol (13.911 g, 0.1 mol) in 100 ml of DMF. The mixture was heated at 60° C. for 1 h (no evolution of hydrogen) and then cooled to room temperature. To this mixture was added dropwise ethyl-4-bromobutyrate (23.4 g, 0.12 mols) in 50 ml of DMF over a period of 15 mins. The mixture was again heated at 60° C. and stirred for 4 hrs. After cooling to room temperature, the solvents were evaporated under reduced pressure. 150 ml water was added to the crude product which was then extracted using ethyl acetate (2×150 ml). The combined organic layers were washed with brine, dried and filtered. The solvent was removed in vacuo and the residue purified by flash chromatography (90% hexane/10% ethyl acetate v/v) to give 21.7 g (86% yield) of [ethyl-p-(O-carboxypropyl)-1-nitrophenyl] (compound 8) as a white solid.

To a stirring solution of compound 8 (9.87 g, 0.039 mol) in 400 ml of anhydrous methanol was added, under nitrogen, Pd—C (10%)(1.95 g) followed by ammonium formate (15 g, 0.189 mols). The mixture was stirred at room temperature for 2 hours, after which TLC confirmed that all starting materials had been consumed. The catalyst was removed by filtration over Celite™. The solvent was then removed under vacuum and the residue taken up in water (150 ml). The aqueous solution was made alkaline by the addition of 2N sodium hydroxide and extracted by ether (2×150 ml). The organic layers were combined, washed with water (100 ml), brine (100 ml) and dried over anhydrous sodium sulfate. The solution was then concentrated under reduced pressure to give a white solid of compound 9 (6.52 g, 75% yield).

EXAMPLE 13

Reaction Scheme 4

Preparation of N-[(1-phenethyl-4-piperidinyl)-N-(ethyl p-(O-carboxypropyl))]phenylamine (Compound 10)

Compound 10 was prepared in the same manner as outlined in Example 1 using compound 9 instead of aniline and 1-phenethyl-4-piperidone, in the presence of anhydrous 1,2-dichloroethane, acetic acid and sodium triacetoxyborohydride. Compound 10 was obtained in crystal form (65% yield).

EXAMPLE 14

Reaction Scheme 4

Preparation of [ethyl-p-(O-carboxypropyl)]fentanyl (Compound 11)

The title compound was prepared in the same manner as outlined in Example 2, using compound 10 in anhydrous toluene and propionic anhydride under reflux. The title compound 11 was obtained as a white solid in 80% yield.

EXAMPLE 15

Reaction Scheme 4

Preparation of p-[(O-carboxypropyl)]fentanyl (Hapten F)

To a solution of compound 11 (3.5 g, 7.5 mmol) in methanol (80 ml) was added 2N sodium hydroxide (20 ml) and the mixture stirred at room temperature for 4 hours (TLC showed no starting materials were left). The mixture was reduced to dryness in vacuo, water (50 ml) was added and the pH of the resulting solution adjusted to 6. The solution was extracted with chloroform (2×100 ml), the combined organic extracts were washed with brine (1×50 ml), dried over sodium sulfate, filtered and concentrated in vacuo. The solid obtained was triturated with ether, filtered and dried overnight to give 2.1 g (64% yield) of hapten F.

Figure 15:
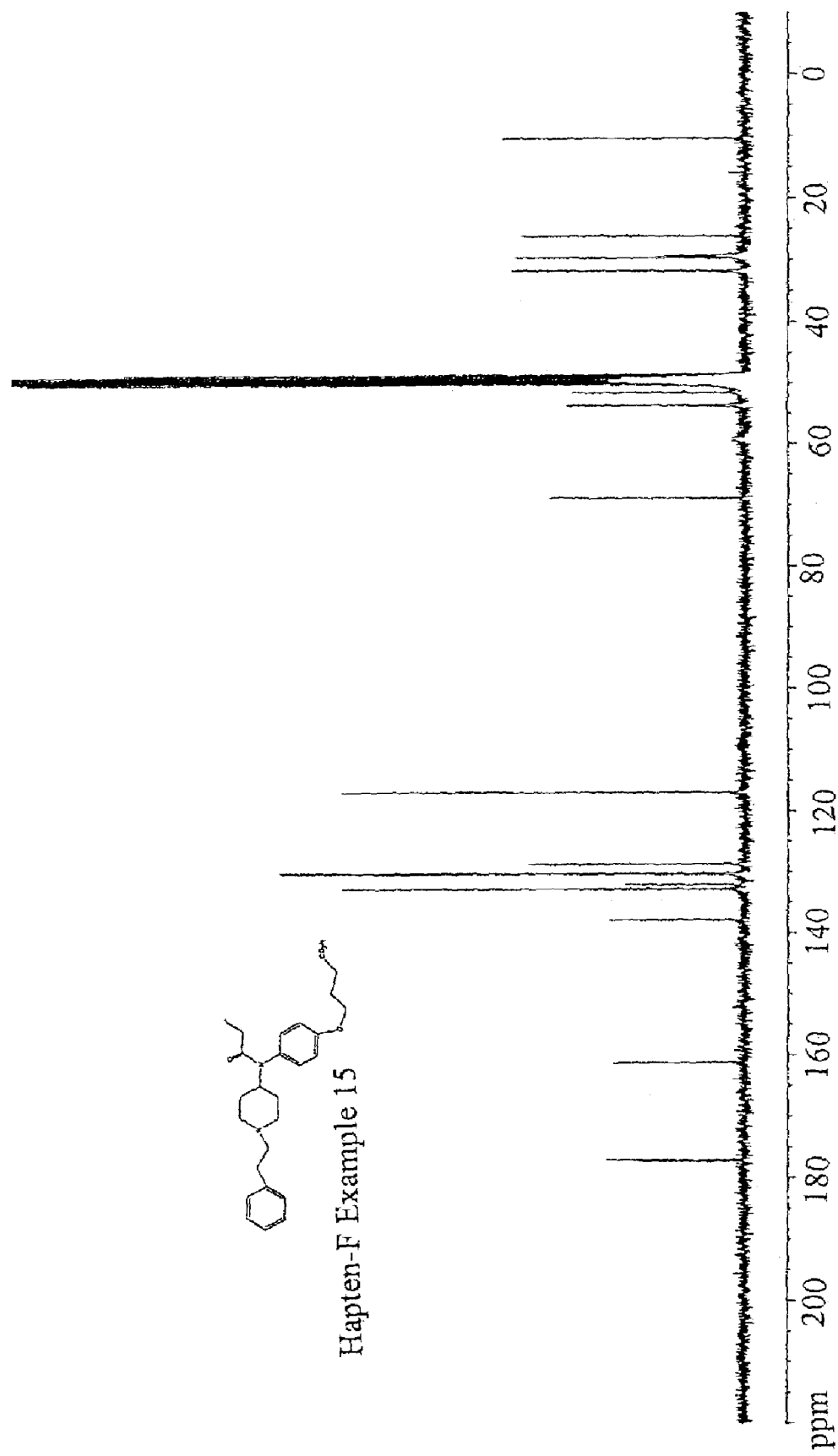
FIG. 15 shows NMR$^{13}$C data for Hapten F.

NMR Data for hapten F are presented in FIG. 15.

EXAMPLE 16

Reaction Scheme 5

Preparation of ethyl (1-carboxymethyl)-4-piperidone (Compound 12)

To a solution of 4-piperidone monohydrate monohydrochloride (12 g, 78.12 mmol) in anhydrous dimethylformamide (120 ml) under nitrogen was added, in small portions, sodium hydride [60% w/w dispersion in mineral oil] (5.25 g, 156 mmol). After complete addition, the mixture was heated at 60° C. for 1 hour (no further hydrogen gas was seen to be evolved), cooled to room temperature and ethyl bromoacetate (19.6 g, 177 mmol) in DMF (50 ml) added dropwise over 15 minutes. The resulting mixture was heated at 60° C. overnight. A few drops of water were added to quench the reaction and the solvents were removed in vacuo. Water (100 ml) was added and the mixture extracted with ethyl acetate (2×100 ml). The combined organic layers were washed with water (1×100 ml), brine (1×100 ml), dried over sodium sulfate and the solvent removed in vacuo. The residue was purified by column chromatography (50% ethyl acetate/50% hexane v/v) to give the title compound 12 as a clear oil (3.4 g, 65% yield).

EXAMPLE 17

Reaction Scheme 5

Preparation of N-[ethyl-1-carboxymethyl)-4-(phenylamino)]piperidine (Compound 13)

The compound 13 was prepared in the same manner as outlined in Example 1, using ethyl (1-carboxymethyl)-4-piperidone (compound 12) (7.4 g, 0.04 mol) and aniline (8.2 g, 0.14 mol) in 1,2-dichloroethane (120 ml) in the presence of sodium triacetoxyborohydride (8.5 g, 0.04 mol) and acetic acid (4 ml). The title compound was obtained after purification by column chromatography (silica gel, 10% v/v methanol in chloroform) (8.4 g, 80% yield).

EXAMPLE 18

Reaction Scheme 5

Preparation of N-(ethyl-carboxymethyl)-norfentanyl (Compound 14)

Compound 14 was prepared from compound 13 (7.86 g, 0.03 mol) in anhydrous toluene and propionic anhydride (8.59 g, 0.066 mol) using the same method as given in Example 2. Compound 14 was obtained after recrystallisation from ethyl acetate/hexane (7.15 g, 75% yield).

EXAMPLE 19

Reaction Scheme 5

Preparation of N-(carboxymethyl)-norfentanyl (Hapten G)

To a solution of compound 14 (3.78 g, 10 mmol) in methanol (80 ml) was added 2N sodium hydroxide (20 ml) and the mixture stirred at room temperature for 4 hours (TLC showed no starting materials present). The mixture was reduced to dryness, water (50 ml) was added and the pH adjusted to 5 by addition of 1N HCl. The precipitate which formed was collected by filtration, washed with a little cold water and dried overnight in the presence of phosphorous pentoxide. The white solid obtained corresponds to hapten G (1.38 g, 50 % yield).

Figure 16:
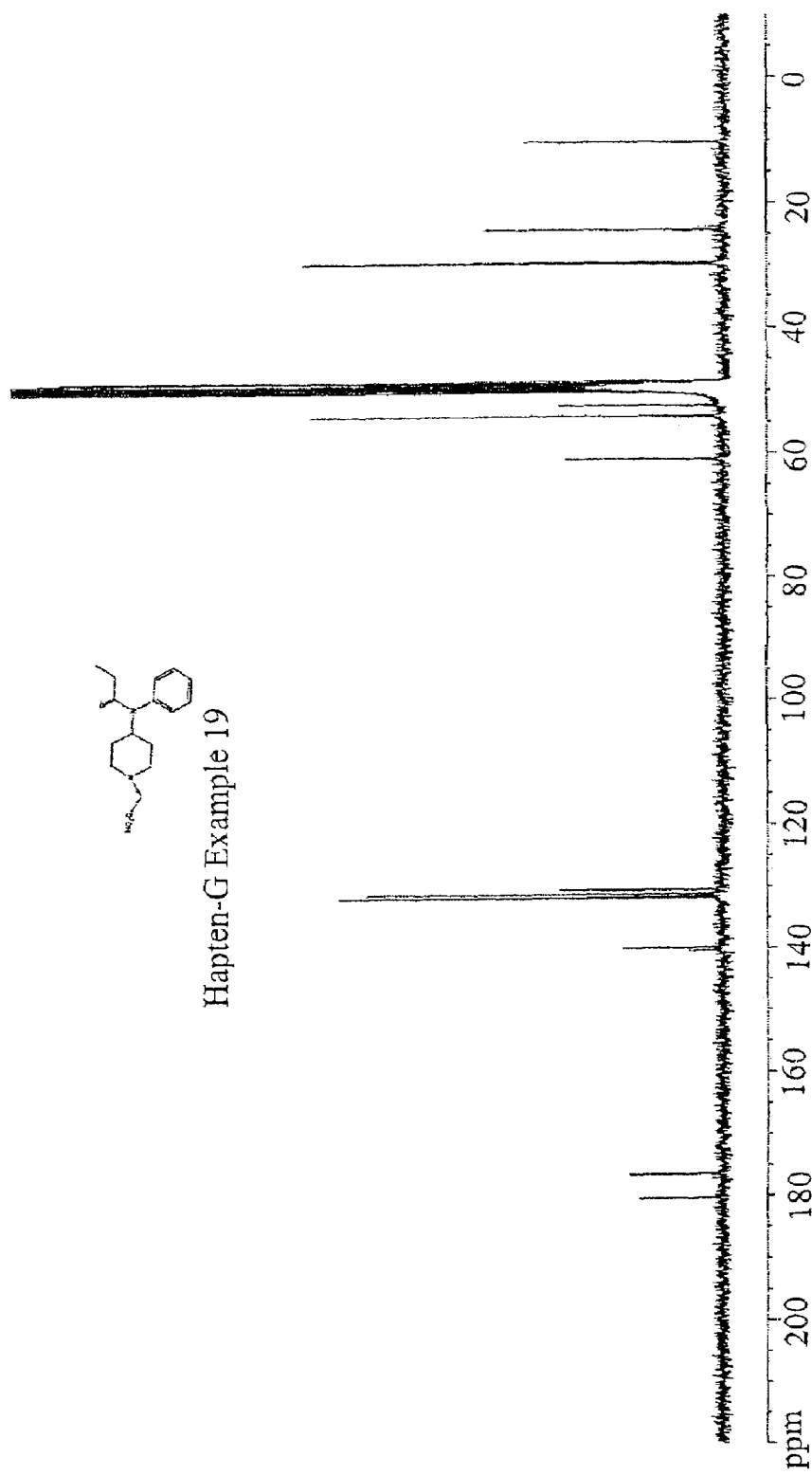
FIG. 16 shows NMR$^{13}$C data for Hapten G.

NMR data for hapten G are presented in FIG. 16.

EXAMPLE 20

Preparation of Bovine Serum Albumin (BSA)—Bromoacetylglycine

To a solution of BSA (1 g) in 0.1M borate buffer (pH 8.5, 45 ml), cooled to 0° C., was added dropwise N-succinimidyl bromoacetylglycine (0.375 g, 0.13 mmol) in DMF (5 ml). During the addition the pH was maintained at 8. After complete addition, the pH was stabilized at 8 and the solution was stirred at 0° C. for one hour. The pH was then adjusted to approximately 7 and the solution dialysed overnight at 4° C. against distilled water (2 changes). The solution was then freeze dried to give approximately 1 g of BSA modified by bromoacetylglycine.

Figure 7:
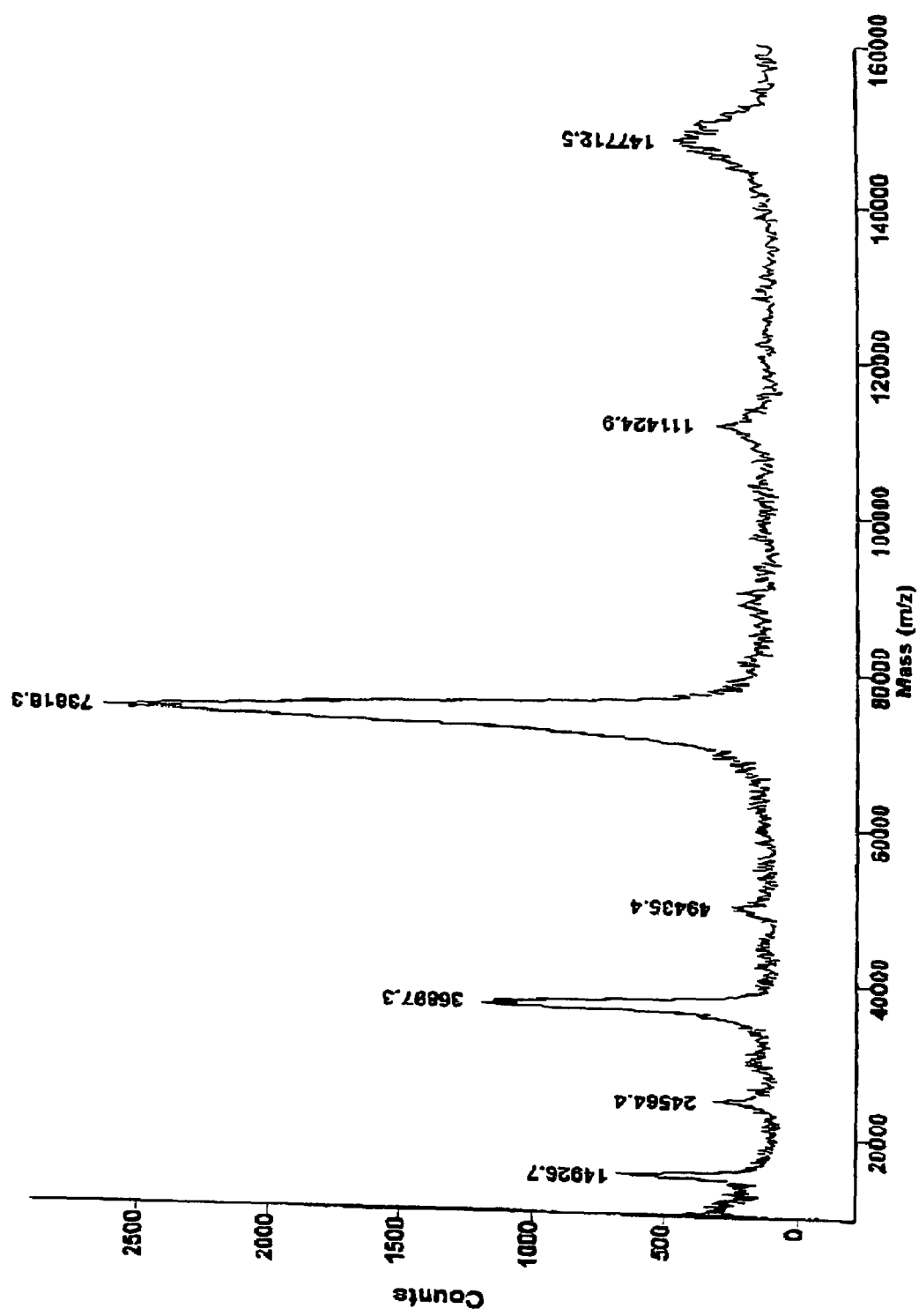
FIG. 7 shows MALDI-TOF analysis of bromoacetyl modified BSA carrier material.

MALDI-TOF analysis (see FIG. 7) shows that a major signal was present which indicates an average protonated mass for this sample of m/z 73,818. The signals at m/z 24,564, 36,897 and 147,713 are consistent with the major component in triply-charged, doubly-charged and dimer forms respectively. Further signals were observed including those at m/z 14,927, 49,425 and 111,425.

These data suggest that 40.3 lysine groups per molecule of BSA have been modified by the bromoacetylglycine.

EXAMPLE 21

Production of Immunogen A Using Bromoacetylglycine Modified BSA

Hapten A (58.15 mg, 0.12 mmol) was dissolved in anhydrous DMF (100 μL) and to this solution was added hydroxylamine solution (900 μL, pH 12). The mixture was allowed to stand 10–15 mins (TLC showed disappearance of Hapten A and the formation of a new compound of lower Rf). Phosphate buffer was added to quench the reaction and the pH adjusted to 7 by the addition of 0.5M HCl. This solution was added dropwise to a solution of the modified BSA of Example 20 (200 mg in 10 ml of water) and the solution stirred at 4° C. overnight (protected from light). The solution was then dialysed against distilled water for 24 hours (3 changes) and freeze-dried.

Figure 8:
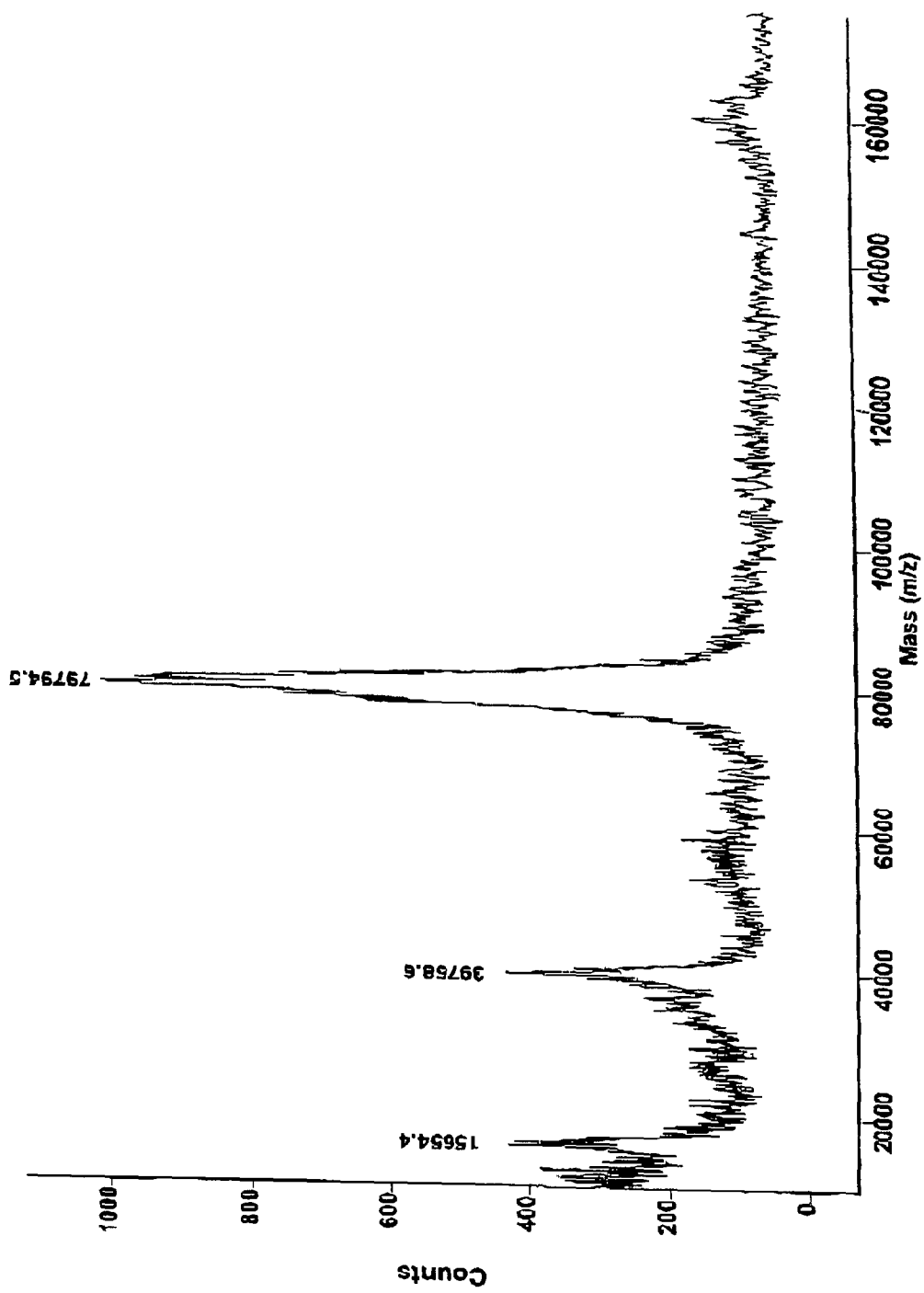
FIG. 8 shows MALDI-TOF analysis of Hapten A conjugated to bromoacetyl modified BSA carrier material.

MALDI results (see FIG. 8 of the accompanying drawings) showed 12.5 molecules of Hapten A had been conjugated to one molecule of modified BSA. Specifically, a signal was present which indicates an average protonated mass for this sample of m/z 79,795. The signal at m/s 39,759 is consistent with the major component in doubly-charged form. A further signal was observed at m/z 15,654.

EXAMPLE 22

Production of Immunogen C Using Bromoacetylglycine Modified BSA

The conjugation was carried out by the method given in Example 21 using Hapten C.

Figure 9:
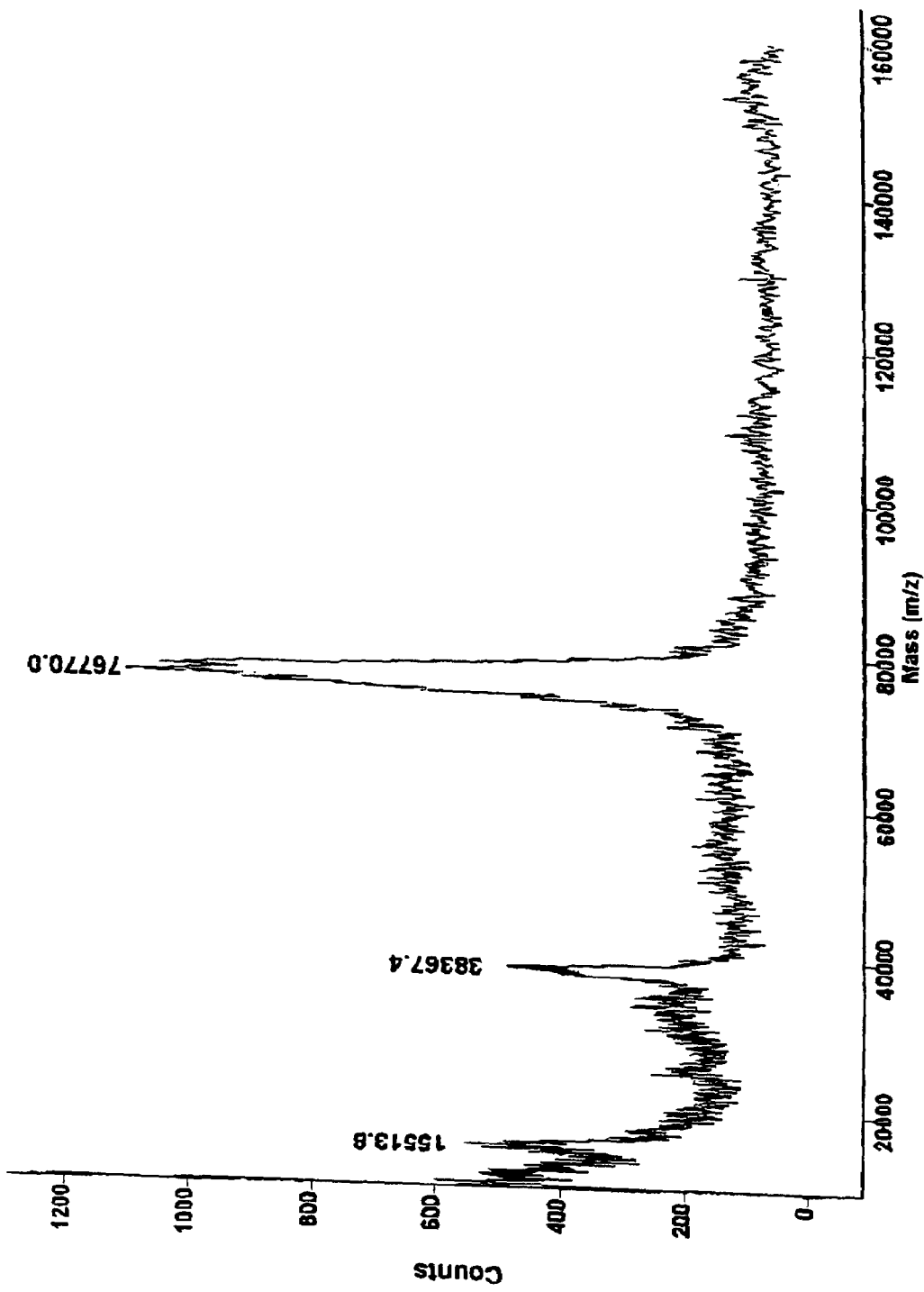
FIG. 9 shows MALDI-TOF analysis of Hapten C conjugated to bromoacetyl modified BSA carrier material.

MALDI results (see FIG. 9 of the accompanying drawings) showed 7.2 molecules of Hapten C had been conjugated to one molecule of modified BSA. Specifically, a major signal was present which indicates an average protonated mass for this sample of m/z 76,770. The signal at m/z 38,367 is consistent with the major component in doubly-charged form. A further signal was observed at m/z 15,514.

EXAMPLE 23

Reaction Scheme 4

Production of Immunogen F using BSA 50 mg 1-ethyl-3-(3-dimethylaminopropyl)carbodiimide hydrochloride (EDC) was dissolved in 600 μl water and immediately added to a solution of 100 mg BSA (1.5 μmol) in 4 ml water. Hapten F (19.7 mg, 45 μmol) dissolved in 2 ml anhydrous DMF was added dropwise, with stirring. 5 mg sulfo-NHS was added and the resulting solution was incubated overnight at 37° C. The solution was then dialysed against 5 L phosphate buffered saline (PBS), pH7.2, for 24 hours at 4° C., with stirring.

Figure 10:
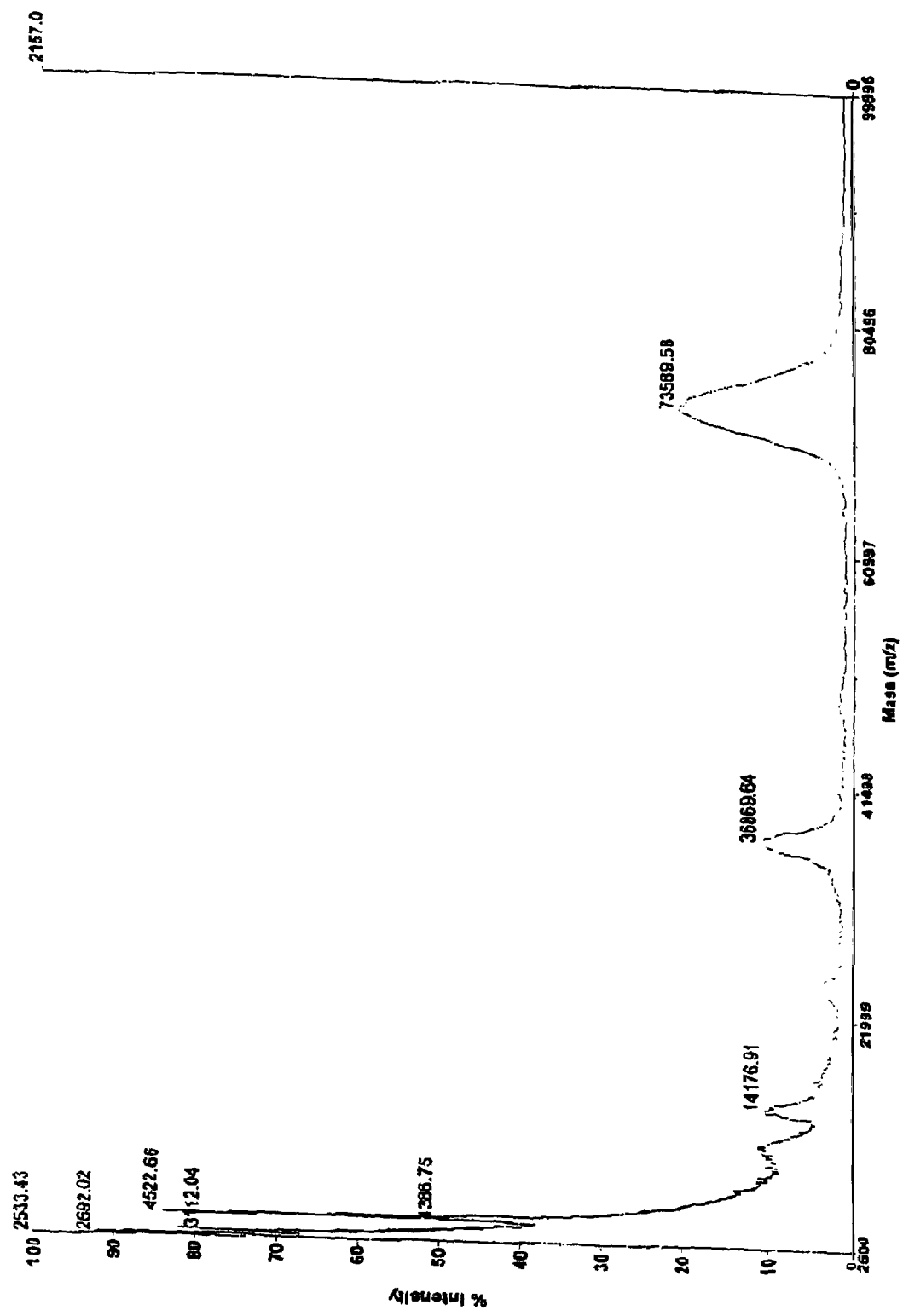
FIG. 10 shows MALDI-TOF analysis of Hapten F conjugated to BSA carrier material.

MALDI results (see FIG. 10 of the accompanying drawings) showed 17.1 molecules of hapten F had been conjugated to one molecule of BSA. Specifically, a major signal was present which indicates an average protonated mass for this sample of m/z 73,590. The signal at m/z 36,870 is consistent with the major component in a doubly-charged form. Further signals were observed including that at m/z 14,177.

EXAMPLE 24

Reaction Scheme 5

Production of Immunogen G using BSA

This conjugation was performed by the method outlined in Example 23 using hapten G (12.57 mg, 431 mol).

Figure 11:
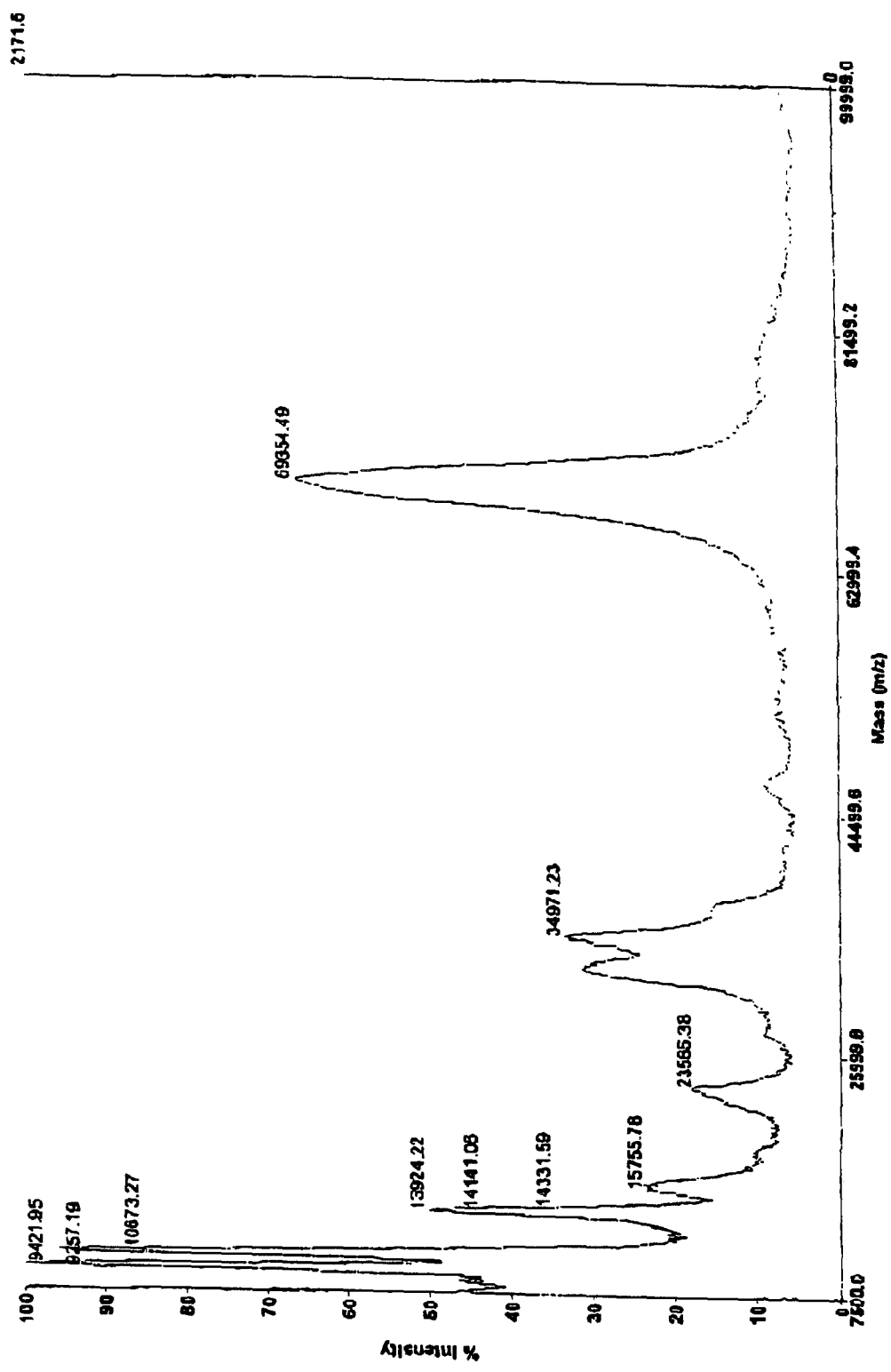
FIG. 11 shows MALDI-TOF analysis of Hapten G conjugated to BSA carrier material.

MALDI results (see FIG. 11 of the accompanying drawings) showed 10.4 molecules of hapten G had been conjugated to one molecule of BSA. Specifically, a major signal was present which indicates an average protonated mass for this sample of m/z 69,355. The signal at m/z 34,971 is consistent with the major component in a doubly-charged form. Further signals were observed including that at m/z 13,924.

EXAMPLE 25

Conjugation of Haptens B and E to Labelling Agent (Horse Radish Peroxidase (HRP))

10 mg of EDC was dissolved in 800 μl water and immediately added to a solution of the hapten (1 mg) in 200 μl DMF. The resulting solution was mixed gently and then added to a solution of HRP (20 mg) in 1 ml water. After mixing, 5 mg of sulfo-NHS was added and the entire reaction was incubated overnight at 37° C. in the dark. The resulting conjugate was purified by passage through two PD10 columns (Pharmacia Biotech), eluted with 20 mM PBS, pH 7.2, and then dialysed overnight at 4° C. against 20 mM PBS, pH 7.2.

EXAMPLE 26

Conjugation of Hapten G to Labelling Agent (HRP)

10 μl triethylamine (TEA) was added to a solution of Hapten G (1 mg) in 400 μl DMF and the resulting solution was mixed for 10 minutes at room temperature. 4 μl isobutylchloroformate (BCF) was then added and allowed to react for a further 10 minutes at room temperature. The activated hapten was immediately added to a solution of HRP (20 mg) in 2 ml water and the reaction was incubated overnight, with mixing, at room temperature in the dark. The resulting conjugate was purified by passage through two PD10 columns (Pharmacia Biotech), eluted with 20 mM PBS, pH 7.2, and then dialysed overnight at 4° C. against 20 mM PBS, pH 7.2.

EXAMPLE 27

Immunisation and Bleeding

An aqueous solution of each of the immunogens prepared in Examples 21, 22, 23 and 24 was formulated with Freund's Complete Adjuvant (FCA) to form an emulsion consisting of 2 mg/ml immunogen in 50% (v/v) FCA. Three sheep were immunized with this emulsion, 0.25 ml being subcutaneously injected at each of four sites in the flank of each animal. Subsequent immunisations (boosts) contained 1 mg/ml immunogen emulsified in 50% (v/v) Freund's Incomplete Adjuvant (FIA) and were administered in the same manner at monthly intervals for 1 year. Blood sampling took place 7 to 14 days after each boost. Each sample was processed to produce antiserum, which was further purified by caprylic acid and ammonium sulfate precipitation to yield an immunoglobulin G (IgG) fraction. The IgG fraction was evaluated by competitive ELISA microtiter plate assay, as described below.

EXAMPLE 28

Competitive ELISA Microtiter Plate Assays for Nor Fentanyl and Fentanyl.

Figure 12:
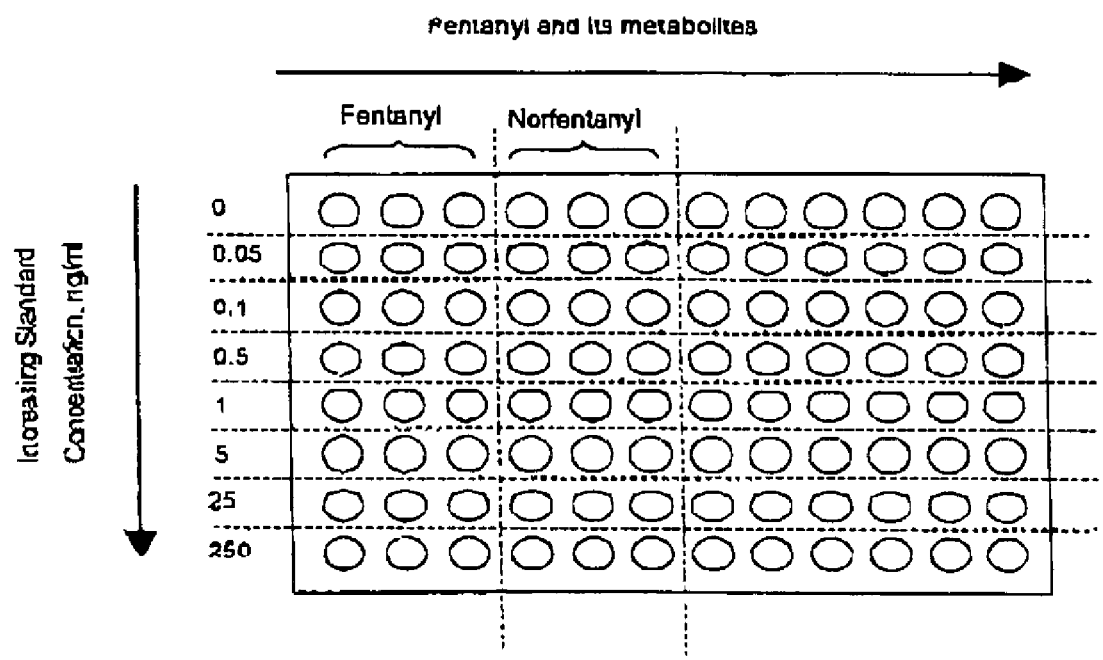
FIG. 12 shows a competitive ELISA microtiter plate.

(a) The wells of an enhanced binding 96 well polystyrene microtiter plate were coated with the IgG fraction of the antiserum raised to Immunogen A (Hapten A-BSA) (Example 21), diluted in 10 mM Tris, pH 8.5 (125 μl/well). The appropriate antibody coating dilution was determined using standard ELISA chequerboard techniques. The plate was incubated for 2 hours at 37° C., washed 4 times with Tris buffered saline containing Tween 20 (TBST) and tapped dry. Standard solutions of fentanyl and norfentanyl were prepared in TBST at 0, 1, 5, 10, 50 and 500 ng/ml and 25 μl of each was added to the appropriate wells (see FIG. 12). 100 μl of conjugate B (hapten B-HRP) (Example 25), diluted in Tris buffer containing EDTA, D-mannitol, sucrose, thimerosal and BSA, was added to each of the wells, as shown in FIG. 12. The appropriate dilution of conjugate was also determined using standard ELISA chequerboard techniques. The plate was incubated at 37° C. for 2 hours. The excess unbound conjugate was removed by washing 6 times over a 10 minute period with TBST. 125 μl of tetramethylbenzidine (TMB) substrate solution was added to each well of the plate, which was then incubated for 15 to 20 minutes in the dark at room temperature. The reaction was terminated by addition of 125 μl 0.2M $H_2SO_4$ to each well. The absorbance was then measured at 450 nm using a microtiter plate reader. The data generated in the assay is presented in Table 1 below.

TABLE 1

Data generated from a competitive microtiter plate assay for norfentanyl and fentanyl employing antiserum raised to immunogen A (hapten A-BSA) (Example 21) and conjugate B (hapten B-HRP) as detection reagent (Example 25).

| Standard Concentration | Fentanyl | | Norfentanyl | |
| --- | --- | --- | --- | --- |
| ng/ml | $A_{450}$ | % $B/B_0$ | $A_{450}$ | % $B/B_0$ |
| 0 | 2.3 | | 2.29 | |
| 0.05 | 2.07 | 90.15 | 2.18 | 94.94 |
| 0.1 | 1.84 | 80.2 | 2.11 | 91.83 |
| 0.5 | 1.26 | 54.91 | 1.94 | 84.57 |
| 1 | 0.87 | 38.01 | 1.77 | 77.27 |
| 5 | 0.27 | 11.74 | 1.37 | 59.8 |
| 25 | 0.08 | 3.68 | 0.76 | 33.32 |
| 250 | 0.08 | 3.53 | 0.24 | 10.57 |
| $IC_{50}$ | 0.61 ng/ml | | 9.07 ng/ml | |

$A_{450}$ = absorbance at 450 nm
B = absorbance at 450 nm at xng/ml standard concentration
$B_0$ = absorbance at 450 nm at 0 ng/ml standard concentration
$IC_{50}$ = standard concentration which produces 50% $B/B_0$ (b) In a similar manner to that described in Example 28(a) and using the same definitions for $A_{450}$, B, $B_0$ and $IC_{50}$, the wells of a 96 well microtiter plate were coated with the IgG fraction of the antiserum raised to immunogen A (hapten A-BSA) (Example 21) and conjugate G (hapten G-HRP) (Example 26) was employed as detection reagent. The data generated is presented in Table 2 below.

TABLE 2

Data generated from a competitive microtiter plate assay for norfentanyl and fentanyl employing antiserum raised to immunogen A (hapten A-BSA) (Example 21) and conjugate G (hapten G-HRP) as detection reagent (Example 26).

| Standard Concentration | Fentanyl | | Norfentanyl | |
| --- | --- | --- | --- | --- |
| ng/ml | $A_{450}$ | % $B/B_0$ | $A_{450}$ | % $B/B_0$ |
| 0 | 1.99 | | 1.94 | |
| 0.05 | 1.94 | 97.09 | 1.85 | 95.69 |
| 0.1 | 1.94 | 97.54 | 1.82 | 93.93 |
| 0.5 | 1.71 | 85.9 | 1.67 | 86.31 |
| 1 | 1.47 | 73.66 | 1.52 | 78.48 |
| 5 | 0.4 | 19.97 | 1.03 | 53.04 |
| 25 | 0.07 | 3.54 | 0.56 | 29.14 |
| 250 | 0.03 | 1.43 | 0.14 | 7.05 |
| $IC_{50}$ | 2.03 ng/ml | | 6.14 ng/ml | |

(c) In a similar manner to that described in Example 28(a), the wells of a 96 well microtiter plate were coated with the IgG fraction of the antiserum raised to immunogen C (hapten C-BSA) (Example 22) and conjugate E (hapten E-HRP) (Example 25) was employed as detection reagent. The data generated is presented in Table 3 below.

TABLE 3

Data generated from a competitive microtiter plate assay for norfentanyl and fentanyl employing antiserum raised to immunogen C (hapten C-BSA) (Example 22) and conjugate E (hapten E-HRP) as detection reagent (Example 25).

| Standard Concentration ng/ml | Fentanyl $A_{450}$ | Fentanyl % $B/B_0$ | Norfentanyl $A_{450}$ | Norfentanyl % $B/B_0$ |
|---|---|---|---|---|
| 0 | 2.3 | | 2.2 | |
| 0.05 | 1.9 | 82.2 | 2.1 | 94.3 |
| 0.1 | 1.6 | 68.2 | 2.0 | 90.8 |
| 0.5 | 0.8 | 34.4 | 1.9 | 88.5 |
| 1 | 0.5 | 23.4 | 1.9 | 88.6 |
| 5 | 0.2 | 8.4 | 1.9 | 89.2 |
| 25 | 0.1 | 2.8 | 2.0 | 90.1 |
| 250 | 0.0 | 1.0 | 2.0 | 89.6 |
| $IC_{50}$ | | 0.24 ng/ml | | >250 ng/ml |

The invention claimed is:

1. An immunogen of the formula:

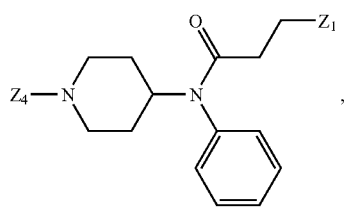

wherein $Z_1$ is hydrogen; and $Z_4$ is selected from the group consisting of a crosslinker coupled to an antigenicity-conferring carrier material and

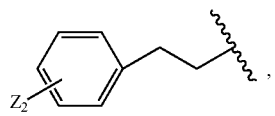

wherein $Z_2$ is a crosslinker coupled to an antigenicity-conferring carrier material at an ortho, a meta or a para position.

2. The immunogen of claim 1, wherein the crosslinker of $Z_2$ is at the para position.

3. The immunogen of claim 1, wherein the crosslinker terminates, at its free end, with —CO—R, in which R is selected from the group consisting of hydroxyl and a short chain ($C_{1-5}$) alkyl moiety.

4. The immunogen of claim 3, wherein R is a short chain ($C_{1-2}$) alkyl moiety.

5. The immunogen of claim 1, wherein the crosslinker comprises:

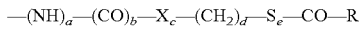

wherein, independently, a is 0 or 1; b is 0 or 1; X is oxygen or sulfur; c is 0 or 1; d is selected from the integers 1–5; e is 0 or 1 and R is selected from the group consisting of a short chain alkyl ($C_{1-5}$) moiety and a hydroxyl moiety or a, b, c and d are 0, e is 1 and R is methyl.

6. The immunogen of claim 1, wherein the crosslinker comprises:

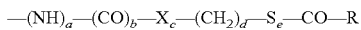

wherein, independently, a is 0 or 1; b is 0 or 1; X is oxygen or sulfur; c is 0 or 1; d is selected from the integers 0–5; e is 0 or 1 and R is selected from the group consisting of a short chain alkyl ($C_{1-5}$) moiety and a hydroxyl moiety.

7. The immunogen of claim 5 or 6, wherein R is a short chain alkyl ($C_{1-2}$) moiety.

8. The immunogen of claim 5 or 6, wherein a is 1; b is 1; c is 0; and d is 2.

9. The immunogen of claim 8, wherein e is 1; and R is methyl.

10. The immunogen of claim 8, wherein e is 0; and R is hydroxyl.

11. The immunogen of claim 9, wherein $Z_1$ is hydrogen and the $Z_2$ crosslinker is at the para position.

12. The immunogen of claim 10, wherein $Z_1$ is hydrogen and the $Z_2$ crosslinker is at the para position.

13. The immunogen of claim 5 or 6, wherein a is 0; b is 0; and c is 0.

14. The immunogen of claim 13, wherein d is 0; e is 1 and R is methyl.

15. The immunogen of claim 13, wherein d is 1; e is 0; and R is hydroxyl.

16. The immunogen of claim 14, wherein $Z_4$ is the crosslinker coupled to the antigenicity-conferring carrier material.

17. The immunogen of claim 14, wherein $Z_4$ is the crosslinker coupled to the antigenicity-conferring carrier material.

18. The immunogen of claim 1, in which the antigenicity-conferring carrier material is selected from the group consisting of a protein, a protein fragment, a synthetic polypeptide and a semi-synthetic polypeptide.

19. The immunogen of claim 6, wherein d is 0 or 1; e is 0; and R is hydroxyl.

20. Antibodies raised against the immunogen of claim 1, wherein the antibodies are capable of binding with at least one structural epitope of a metabolite of fentanyl or of a metabolite of a fentanyl analog.

21. Antibodies raised against the immunogen of claim 18, wherein the antibodies are capable of binding with at least one structural epitope of a metabolite of fentanyl or of a metabolite of a fentanyl analog.

22. A process of preparing the antibodies as claimed in claim 20, the process comprising the steps of immunising an animal by repeated administration of the immunogen of claim 1, and collecting the resulting serum from the immunised animal.

23. A process of preparing the antibodies as claimed in claim 21, the process comprising the steps of immunising an animal by repeated administration of the immunogen of claim 18, and collecting the resulting serum from the immunised animal.

24. A conjugate of the formula:

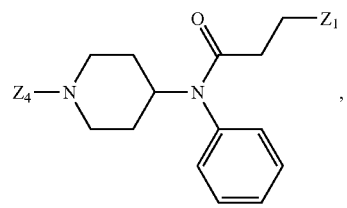

wherein $Z_1$ is hydrogen; $Z_4$ is selected from the group consisting of a crosslinker covalently bonded to a labelling agent which is detectable and

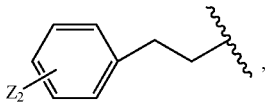

wherein $Z_2$ is a crosslinker covalently bonded to a labelling agent which is detectable at an ortho, a meta or a para position.

25. The conjugate of claim 24, wherein the crosslinker comprises:

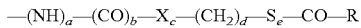

wherein, independently, a is 0 or 1; b is 0 or 1; X is oxygen or sulfur; c is 0 or 1; d is selected from the integers 0–5; e is 0 or 1 and R is selected from the group consisting of a short chain alkyl ($C_{1-5}$) moiety and a hydroxyl moiety.

26. The conjugate of claim 25, wherein d is 0 or 1; e is 0; and R is hydroxyl.

27. The conjugate of claim 24, wherein the crosslinker of $Z_2$ is at the para position.

28. The conjugate of claim 24, wherein the crosslinker terminates, at its free end, with —CO—R, in which R is selected from the group consisting of hydroxyl and a short chain alkyl ($C_{1-5}$) moiety.

29. The conjugate of claim 28, wherein R is a short chain ($C_{1-2}$) alkyl moiety.

30. The conjugate of claim 24, wherein the crosslinker comprises:

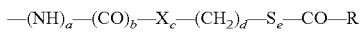

in which, independently, a is 0 or 1; b is 0 or 1; X is oxygen or sulfur; c is 0 or 1; d is selected from the integers 1–5; e is 0 or 1 and R is selected from the group consisting of a short chain alkyl ($C_{1-5}$) moiety and a hydroxyl moiety or a, b, c and d are 0, e is 1 and R is methyl.

31. The conjugate of claim 30 or 25, wherein R is a short chain ($C_{1-2}$) alkyl moiety.

32. The conjugate of claim 30 or 25, wherein a is 1; b is 1; c is 0; and d is 2.

33. The conjugate of claim 32, wherein e is 1; and R is methyl.

34. The conjugate of claim 32, wherein e is 0; and R is hydroxyl.

35. The conjugate of claim 33, wherein $Z_1$ is hydrogen and the $Z_2$ crosslinker is at the para position.

36. The conjugate of claim 34, wherein $Z_1$ is hydrogen and the $Z_2$ crosslinker is at the para position.

37. The conjugate of claim 30 or 25, wherein a is 0; b is 0; and c is 0.

38. The conjugate of claim 37, wherein d is 0; e is 1 and R is methyl.

39. The conjugate of claim 37, wherein d is 1; e is 0; and R is hydroxyl.

40. The conjugate of claim 38, wherein $Z_4$ is the crosslinker covalently bonded to the labelling agent which is detectable.

41. The conjugate of claim 39, wherein $Z_4$ is the crosslinker covalently bonded to the labelling agent which is detectable.

42. The conjugate of claim 24, wherein the detectable labelling agent is selected from the group consisting of an enzyme; a luminescent substance; and a radioactive substance; or a mixture thereof.

43. The conjugate of claim 42, in which the enzyme is a peroxidase or a mixture thereof.

44. The conjugate of claim 42, in which the luminescent substance is selected from the group consisting of a bioluminescent substance, a chemiluminescent substance and a fluorescent substance, or a mixture thereof.

45. A method for detecting, or determining the quantity of, metabolites of fentanyl, or of metabolites of fentanyl analogs in a sample, the method comprising contacting the sample with the conjugate of claim 24, or a mixture thereof and with the antibodies of claim 20 or a mixture thereof; detecting, or determining the quantity of, bound conjugate; and deducing from a calibration curve the presence, or the amount of, metabolites of fentanyl, and metabolites of fentanyl analogs in the sample.

46. The method of claim 45, wherein the antibodies are raised against an immunogen wherein $Z_2$ is the crosslinker coupled to the antigenicity-conferring carrier material.

47. The method of claim 45, wherein $Z_4$ of the conjugate is the crosslinker covalently bonded to the labelling agent which is detectable.

48. A kit for detecting, or determining the quantity of, metabolites of fentanyl, or metabolites of fentanyl analogs, the kit including the conjugate of claim 24 or a mixture thereof and the antibodies of claim 20 or a mixture thereof.

49. The kit of claim 48, in which the antibodies are raised against an immunogen wherein $Z_2$ is the crosslinker coupled to the antigenicity-conferring carrier material.

50. The kit of claim 48, wherein $Z_4$ of the conjugate is the crosslinker covalently bonded to the labelling agent which is detectable.

* * * * *